US011998310B2

(12) United States Patent
Liu et al.

(10) Patent No.: US 11,998,310 B2
(45) Date of Patent: *Jun. 4, 2024

(54) MEDICAL DEVICE WITH MULTI-CORE FIBER FOR OPTICAL SENSING

(71) Applicant: St. Jude Medical International Holding S.à r.l., Luxembourg (LU)

(72) Inventors: Yu Liu, Irvine, CA (US); John W. Sliwa, San Jose, CA (US); Jiayin Liu, Laguna Hills, CA (US); Giovanni Leo, Cologny (CH); Troy T. Tegg, Elk River, MN (US)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 28 days.

This patent is subject to a terminal disclaimer.

(21) Appl. No.: 17/819,247

(22) Filed: Aug. 11, 2022

(65) Prior Publication Data
US 2023/0031938 A1 Feb. 2, 2023

Related U.S. Application Data

(63) Continuation of application No. 15/400,655, filed on Jan. 6, 2017, now Pat. No. 11,445,937.
(Continued)

(51) Int. Cl.
*A61B 5/06* (2006.01)
*A61B 5/00* (2006.01)
(Continued)

(52) U.S. Cl.
CPC ............ *A61B 5/065* (2013.01); *A61B 5/0245* (2013.01); *A61B 5/6852* (2013.01);
(Continued)

(58) Field of Classification Search
CPC ......... A61B 5/042; A61B 5/103; A61B 5/117; A61B 5/6852; A61B 5/6855;
(Continued)

(56) References Cited

U.S. PATENT DOCUMENTS 4,757,194 A 7/1988 Simms
4,918,492 A 4/1990 Ferdinand et al.
(Continued)

FOREIGN PATENT DOCUMENTS

CN 103607961 A 2/2014
CN 105228514 A 1/2016
(Continued)

OTHER PUBLICATIONS

Calkins, et al., "HRS/EHRA/ECAS Expert Consensus Statement on Catheter and Surgical Ablation of Atrial Fibrillation: Recommendations of Personnel, Policy, Procedures and Follow-up", Eurospace (2007) 9, 335-379.
(Continued)

*Primary Examiner* — Eun Hwa Kim
(74) *Attorney, Agent, or Firm* — Armstrong Teasdale LLP

(57) ABSTRACT

A medical device, system, and method having a flexible shaft and a multi-core fiber within the flexible shaft. The multi-core fiber includes a plurality of optical cores dedicated for shape sensing sensors, and a plurality of optical cores dedicated for force sensing sensors. A medical device flexing structure assembly can comprise a multi-core fiber comprising a plurality of cores, and a flexing structure comprising at least one slot. Each of the plurality of cores can comprise a fiber Bragg grating, and the flexing structure can be configured to bend in response to a force imparted on the flexing structure.

20 Claims, 9 Drawing Sheets

Related U.S. Application Data

(60) Provisional application No. 62/275,877, filed on Jan. 7, 2016.

(51) Int. Cl.

| | | |
|---|---|---|
| *A61B 5/0245* | (2006.01) | |
| *A61B 18/14* | (2006.01) | |
| *A61M 25/01* | (2006.01) | |
| *G01K 11/3206* | (2021.01) | |
| *G01K 13/20* | (2021.01) | |
| *G01L 1/24* | (2006.01) | |
| *A61B 18/00* | (2006.01) | |
| *A61B 34/20* | (2016.01) | |
| *A61B 90/00* | (2016.01) | |

(52) U.S. Cl.
CPC ..... *A61B 18/1492* (2013.01); *A61M 25/0147* (2013.01); *G01K 11/3206* (2013.01); *G01K 13/20* (2021.01); *G01L 1/246* (2013.01); *A61B 2018/00029* (2013.01); *A61B 2018/00172* (2013.01); *A61B 2018/00351* (2013.01); *A61B 2018/00577* (2013.01); *A61B 2018/00642* (2013.01); *A61B 2018/00791* (2013.01); *A61B 2018/00839* (2013.01); *A61B 2018/00988* (2013.01); *A61B 2018/1465* (2013.01); *A61B 2034/2061* (2016.02); *A61B 2090/064* (2016.02); *A61B 2218/002* (2013.01); *A61B 2562/223* (2013.01); *A61B 2562/225* (2013.01)

(58) Field of Classification Search
CPC .......... A61B 18/492; A61B 2562/0233; A61B 2562/0238; A61B 2562/0257; A61B 2562/0266

See application file for complete search history.

(56) References Cited

U.S. PATENT DOCUMENTS

| | | |
|---|---|---|
| 4,966,597 A | 10/1990 | Cosman |
| 4,983,034 A | 1/1991 | Spillman et al. |
| 5,014,709 A | 5/1991 | Belkhagen et al. |
| 5,018,529 A | 5/1991 | Tenerz et al. |
| 5,065,010 A | 11/1991 | Knute et al. |
| 5,104,392 A | 4/1992 | Kittrell et al. |
| 5,122,137 A | 6/1992 | Lennox |
| 5,174,277 A | 12/1992 | Matsumaru |
| 5,178,153 A | 1/1993 | Einzig et al. |
| 5,201,317 A | 4/1993 | Kanazawa et al. |
| 5,202,939 A | 4/1993 | Belleville et al. |
| 5,279,793 A | 1/1994 | Glass et al. |
| 5,289,256 A | 2/1994 | Gramling |
| 5,321,501 A | 6/1994 | Schuman et al. |
| 5,348,019 A | 9/1994 | Childers et al. |
| 5,392,117 A | 2/1995 | Belleville et al. |
| 5,396,887 A | 3/1995 | Imran |
| 5,409,000 A | 4/1995 | Imran et al. |
| 5,423,807 A | 6/1995 | Milder |
| 5,446,546 A | 8/1995 | Breidenbach et al. |
| 5,575,787 A | 11/1996 | Abela et al. |
| 5,594,819 A | 1/1997 | Narendran et al. |
| 5,622,108 A | 4/1997 | Benedetto et al. |
| 5,633,494 A | 5/1997 | Danisch et al. |
| 5,645,065 A | 7/1997 | Shapiro et al. |
| 5,688,267 A | 11/1997 | Panescu et al. |
| 5,693,043 A | 12/1997 | Kittrell et al. |
| 5,696,863 A | 12/1997 | Kleinerman et al. |
| 5,769,847 A | 6/1998 | Panescu et al. |
| 5,772,590 A | 6/1998 | Webster |
| 5,782,828 A | 7/1998 | Chen et al. |
| 5,798,521 A | 8/1998 | Froggatt |
| 5,807,265 A | 9/1998 | Itoigawa et al. |
| 5,833,688 A | 11/1998 | Sieben et al. |
| 5,844,927 A | 12/1998 | Kringlebotn et al. |
| 5,858,717 A | 1/1999 | Scobey et al. |
| 5,904,658 A | 5/1999 | Niederauer et al. |
| 5,906,614 A | 5/1999 | Stern et al. |
| 5,967,978 A | 10/1999 | Littmann et al. |
| 6,039,743 A | 3/2000 | Quiachon et al. |
| 6,056,436 A | 5/2000 | Singh et al. |
| 6,063,078 A | 5/2000 | Wittkampf |
| 6,066,102 A | 5/2000 | Townsend et al. |
| 6,066,120 A | 5/2000 | Gregory et al. |
| 6,088,088 A | 7/2000 | Fortenberry et al. |
| 6,102,926 A | 8/2000 | Tartaglia et al. |
| 6,113,590 A | 8/2000 | Fischer et al. |
| 6,113,593 A | 9/2000 | Tu et al. |
| 6,120,476 A | 9/2000 | Fung et al. |
| 6,120,520 A | 9/2000 | Saadat et al. |
| 6,129,667 A | 10/2000 | Dumoulin et al. |
| 6,133,593 A | 10/2000 | Boos et al. |
| 6,134,003 A | 10/2000 | Tearney et al. |
| 6,171,275 B1 | 1/2001 | Webster et al. |
| 6,173,091 B1 | 1/2001 | Reich et al. |
| 6,175,669 B1 | 1/2001 | Colston et al. |
| 6,197,023 B1 | 3/2001 | Muntermann et al. |
| 6,210,346 B1 | 4/2001 | Hall |
| 6,217,574 B1 | 4/2001 | Webster et al. |
| 6,226,542 B1 | 5/2001 | Reisfeld et al. |
| 6,246,898 B1 | 6/2001 | Vesely et al. |
| 6,256,090 B1 | 7/2001 | Chen et al. |
| 6,262,822 B1 | 7/2001 | Obhi et al. |
| 6,266,542 B1 | 7/2001 | Stern et al. |
| 6,266,551 B1 | 7/2001 | Osadchy et al. |
| 6,272,371 B1 | 8/2001 | Shlomo et al. |
| 6,276,215 B1 | 8/2001 | Berg et al. |
| 6,310,990 B1 | 10/2001 | Bellemore et al. |
| 6,324,918 B1 | 12/2001 | Gitis et al. |
| 6,370,412 B1 | 4/2002 | Armoundas et al. |
| 6,398,778 B1 | 6/2002 | Gu et al. |
| 6,425,894 B1 | 7/2002 | Brucker et al. |
| 6,451,009 B1 | 9/2002 | Dasilva et al. |
| 6,458,123 B1 | 10/2002 | Brucker |
| 6,466,811 B1 | 10/2002 | Hassett et al. |
| 6,470,205 B2 | 10/2002 | Bosselmann et al. |
| 6,470,286 B1 | 10/2002 | Watts et al. |
| 6,471,710 B1 | 10/2002 | Bucholtz et al. |
| 6,546,271 B1 | 4/2003 | Reisfeld et al. |
| 6,547,780 B1 | 4/2003 | Sinofsky et al. |
| 6,558,378 B2 | 5/2003 | Sherman et al. |
| 6,563,970 B1 | 5/2003 | Bohnert et al. |
| 6,572,804 B2 | 6/2003 | Randall et al. |
| 6,602,242 B1 | 8/2003 | Fung et al. |
| 6,660,001 B2 | 9/2003 | Gregory et al. |
| 6,674,928 B2 | 1/2004 | Johnson et al. |
| 6,695,808 B2 | 2/2004 | Tom |
| 6,701,931 B2 | 3/2004 | Sliwa et al. |
| 6,868,195 B2 | 3/2005 | Fujita et al. |
| 6,898,338 B2 | 5/2005 | Kersey et al. |
| 6,915,048 B2 | 7/2005 | Kersey et al. |
| 6,852,109 B2 | 8/2005 | Winston et al. |
| 6,947,637 B2 | 9/2005 | Smith et al. |
| 6,955,675 B2 | 10/2005 | Jain et al. |
| 6,986,769 B2 | 1/2006 | Nelson et al. |
| 7,050,662 B2 | 5/2006 | Behrmann et al. |
| 7,114,938 B2 | 10/2006 | Chou et al. |
| 7,173,713 B2 | 2/2007 | Xu et al. |
| 7,241,986 B2 | 7/2007 | Wang et al. |
| 7,460,964 B2 | 12/2008 | Mizota et al. |
| 7,466,879 B2 | 12/2008 | Tjin et al. |
| 7,491,957 B2 | 2/2009 | Kitamura et al. |
| 7,903,907 B1 | 3/2011 | Park et al. |
| 8,048,063 B2 | 11/2011 | Aeby et al. |
| 8,075,498 B2 | 12/2011 | Leo et al. |
| 8,157,789 B2 | 4/2012 | Leo et al. |
| 8,182,433 B2 | 5/2012 | Leo et al. |
| 8,622,935 B1 | 1/2014 | Leo |
| 9,151,811 B2 | 10/2015 | Jester et al. |
| 2001/0021843 A1 | 9/2001 | Bosselmann |
| 2002/0041722 A1 | 4/2002 | Johnson et al. |
| 2002/0041723 A1 | 4/2002 | Ronnekleiv |
| 2002/0057859 A1 | 5/2002 | Walter et al. |

(56) References Cited

U.S. PATENT DOCUMENTS

| | | |
|---|---|---|
| 2002/0072680 A1 | 6/2002 | Schock et al. |
| 2004/0082844 A1 | 4/2004 | Vardi et al. |
| 2004/0165810 A1 | 8/2004 | Fujita et al. |
| 2004/0181138 A1 | 9/2004 | Hindricks et al. |
| 2004/0206365 A1 | 10/2004 | Knowlton et al. |
| 2004/0243119 A1 | 12/2004 | Lane et al. |
| 2005/0062979 A1 | 3/2005 | Zhu et al. |
| 2005/0085693 A1 | 4/2005 | Belson et al. |
| 2005/0213870 A1 | 9/2005 | Kersey et al. |
| 2006/0013523 A1 | 1/2006 | Childlers et al. |
| 2006/0045408 A1 | 3/2006 | Jones et al. |
| 2006/0100610 A1 | 5/2006 | Wallace et al. |
| 2006/0133715 A1 | 6/2006 | Belleville et al. |
| 2006/0200049 A1 | 9/2006 | Leo et al. |
| 2006/0263002 A1 | 11/2006 | Pocha et al. |
| 2007/0014490 A1 | 1/2007 | Silverbrook et al. |
| 2007/0041019 A1 | 2/2007 | Schmidt et al. |
| 2007/0043338 A1 | 2/2007 | Moll et al. |
| 2007/0060847 A1 | 3/2007 | Leo et al. |
| 2007/0065077 A1 | 3/2007 | Childers et al. |
| 2007/0151390 A1 | 7/2007 | Blumenkranz et al. |
| 2007/0151391 A1 | 7/2007 | Larkin et al. |
| 2007/0156019 A1 | 7/2007 | Larkin et al. |
| 2007/0265503 A1 | 11/2007 | Schlesinger et al. |
| 2008/0009750 A1 | 1/2008 | Aeby et al. |
| 2008/0294144 A1 | 11/2008 | Leo et al. |
| 2009/0137952 A1 | 5/2009 | Ramamurthy et al. |
| 2009/0138007 A1 | 5/2009 | Govari et al. |
| 2009/0177095 A1 | 7/2009 | Aeby et al. |
| 2009/0287092 A1 | 11/2009 | Leo et al. |
| 2009/0306643 A1 | 12/2009 | Pappone et al. |
| 2009/0306650 A1 | 12/2009 | Govari et al. |
| 2010/0063478 A1 | 3/2010 | Selkee et al. |
| 2010/0087835 A1 | 4/2010 | Blumenkranz et al. |
| 2010/0094163 A1 | 4/2010 | Deladi et al. |
| 2010/0328675 A1 | 12/2010 | Bertholds et al. |
| 2011/0087112 A1 | 4/2011 | Leo et al. |
| 2012/0078138 A1 | 3/2012 | Leo et al. |
| 2012/0132009 A1 | 5/2012 | Prisco |
| 2012/0265102 A1 | 10/2012 | Leo et al. |
| 2012/0265184 A1 | 10/2012 | Sliwa et al. |
| 2013/0090552 A1 | 4/2013 | Ramamurthy et al. |
| 2014/0330269 A1 | 11/2014 | Pappone et al. |
| 2014/0364848 A1 | 12/2014 | Heimbecher et al. |
| 2015/0029511 A1 | 1/2015 | Hooft et al. |
| 2015/0182279 A1 | 7/2015 | Ashton et al. |
| 2016/0334203 A1 | 11/2016 | Cui et al. |

FOREIGN PATENT DOCUMENTS

| | | |
|---|---|---|
| DE | 3020785 A1 | 12/1981 |
| DE | 3828550 A1 | 3/1990 |
| EP | 0281405 | 9/1988 |
| EP | 0934728 | 8/1999 |
| EP | 1858401 A1 | 11/2007 |
| EP | 1909650 A2 | 4/2008 |
| EP | 2047797 B1 | 4/2014 |
| JP | 09297078 A | 11/1997 |
| JP | 10137200 A | 5/1998 |
| JP | 2000227367 A | 8/2000 |
| JP | 2004251779 A | 9/2004 |
| WO | 199004949 | 5/1990 |
| WO | 9729678 A2 | 8/1997 |
| WO | 9732182 | 9/1997 |
| WO | 9738637 A1 | 10/1997 |
| WO | 9819044 A1 | 5/1998 |
| WO | 9945994 A1 | 9/1999 |
| WO | 0133165 A1 | 5/2001 |
| WO | 0174252 A2 | 10/2001 |
| WO | 0219898 A2 | 3/2002 |
| WO | 0219903 A1 | 3/2002 |
| WO | 0223148 A1 | 3/2002 |
| WO | 0247751 A2 | 6/2002 |
| WO | 2004002303 A1 | 1/2004 |
| WO | 2005059510 A2 | 6/2005 |
| WO | 2006092707 A1 | 9/2006 |
| WO | 2007015139 A3 | 4/2007 |
| WO | 2007050960 A2 | 5/2007 |
| WO | 2007111737 A2 | 10/2007 |
| WO | 2008000246 A2 | 1/2008 |
| WO | 2008003307 A2 | 1/2008 |
| WO | 2008045958 A2 | 4/2008 |
| WO | 2009114955 A1 | 9/2009 |
| WO | 2015106621 A1 | 7/2015 |

OTHER PUBLICATIONS

Cappato, et al., "Worldwide Survey on the Methods, Efficacy, and Safety of Catheter Ablation for Human Atrial Fibrillation", Journal of the American Heart Association, 2005, 7 pgs.

Peirs, et al., "A micro optical force sensor for force feedback during minimally invasive robotic surgery", Sensors and Actuators A 115, 2004, 447-455.

Del Villar, et al., "Optimization of Sensitivity in Long Period Fiber Gratings with Overlay Deposition", Optic Express, vol. 13, No. 1, Jan. 10, 2005, 56-69.

Dickmann, "Experiment 03, Fabry Perot Resonator", 2003, 1-19.

Dupont, "DuPont Zenite LCP liquid crystal polymer resin", Product and Property Guide, K-15415, May 2006. 35 pgs.

Erdemir, et al., "Fiberoptic Measurement of Tendon Forces is Influenced by Skin Movement Artifact", Journal of Biomechanics, vol. 36, No. 3, 449-455, Mar. 2003.

Rao, "Recent progress in applications of in-fibre Bragg grating sensors", Optics and Lasers in Engineering Elseiver UK, vol. 31, No. 4, Apr. 1999, 297-324.

Schmidt, et al., "Fiber-Optic Extrinsic Fabry-Perot Interoferometer Strain Sensor with <50 pm Displacement Resolution Using Three-Wavelength Digital Phase Demodulation", Optic Express, vol. 8, No. 8, Apr. 9, 2001, 475-480.

Shah, et al., "Evaluation of a New Catheter Sensor for Reel-Time Measurement of Tissue Contact", Heart Rhythm Society, vol. 3, Issue 5 (Supplement), S75-576, AB36-6, May 2006, 1 pg.

Van Uffelen, et al. "Anchoring points for fibre optic strain sensors". Optical Techniques for Smart Structures and Structural Monitoring. 1 pg. Feb. 17, 1997.

Xiao, et al. "Fiber optic pressure sensor with self-compensation capability for harsh environment applications". Optical Engineering 44(5), 054-403, XP-002527158. May 2005. 10 pgs.

Fearn, et al., "An Optical Transducer for Single Myofibril Force Measurement", IEEE Transaction on Biomedical Engineering, vol. 40, No. 11, 1993, 1127-1132.

FISO, "FOS-N Strain Sensor", FISO Technologies Inc. Canada, 2006, 2 pgs.

Fuster, et al., "ACC/AHA/ESC 2006 Guidelines for the Management of Patents with Atrial Fibrillation", Circulation Journal of the American Heart Association, 2006, e319-e321.

Hasin, et al., "Miniature Force Transducer for Myocardial Stimulation and Local Tension Measurements", IEEE Transactions on Biomedical Engineering, vol. BME-26, No. 2, Feb. 1979, 104-105.

Inaudi, "Application of optical fiber sensor in civil structural monitoring", Proceedings of the SPIE—The International Society for Optical Engineering SPIE—Int. Soc. Opt. Eng USA, vol. 4328, 2001, 1-10.

Yokoyama, et al. "Novel Radiofrequency Ablation Catheter with Contact Force Sensor Predicts Lesion Size and Incidence of Steam Pop in Canine Model". Heart Rhythm Society, vol. 4, Issue 5 (Supplement), S340-S341, P05-106. 1 pg. May 2007.

Zhang, et al. "On SDM/WDM FBG Sensor Net for Shape Detection of Endoscope".Proceedings of the IEEE, International Conference on Mechatronics and Automation, Niagra Falls, Canada. Jul. 2005. pp. 1986-1991.

Meller, "Extrinsic Fabry-Perot Interferometer System Using Wavelength Modulated Source", Dec. 1996, 57 pgs.

Komi, et al., "Optic Fibre as a Transducer of Tendomuscular Forces", European Journal of Applied Physiology and Occupational Physiology, Vo. 72, No. 3, 1996, 278-280.

(56) References Cited

OTHER PUBLICATIONS

Brown, "Development of Biollouin Scattering Based Distributed Fiber-Optic Strain Sensor", The University of New Brunswick, 2001. 2 pgs.
Lo, "Using in-fiber Bragg-grating sensors for measuring axial strain and temperature simultaneously on surfaces of structures", Optical Engineering, vol. 37, Aug. 1998, 2272-2276.
Luna Innovations, "EFPI Techniques for Strain and Displacement Sensing", Rec. C, Aug. 1999, 6 pgs.
Luna Innovations, "Fiber Optic Bragg Grating Sensor", www.lunainnovations.com/products/shape.asp, Aug. 2005, 18 pgs.
"Endosense achieves ISO 13485 certification", Aug. 12, 2008, 1 pg.
"Endosense launches TOCCATA clinical study", Multi-center European Safety Study on Groundbreaking Technology for the Treatment of Atrial Arrhythmias, Oct. 7, 2008, 1 pg.
"Endosense receives CE mark for Tacticath force-sensing ablation catheter", May 4, 2009, 1 pg.
"Endosense unveils five groundbreaking abstracts on contact force measurement for catheter ablation", May 13, 2008, 1 pg.
"IntelliSense Fine Force Technology", Hansen Medical (website) http://www.hansenmedical.com/products/intellisense.aspx, Sep. 22, 2009, 1 pg.
Natale, et al., "Venice Chart International Consensus Document on Atrial Fibrillation Ablation", Journal of Cardiovascular Electrophysiology, vol. 18, No. 5, 2007, 560-580.
Paris-Seely, et al., "A Compliance-Independent Pressure Transducer for Biomedical Device-Tissue Interfacesm", Biomedical Instrumentation & Technology, vol. 34, No. 6, Nov.-Dec. 2000, 423-31.
"Precision Photonics Corporation", Basic Physics and Design of Etalons, 2003, 1-5.
"Sensei X Robotic Catheter System for Electrophysiology Procedures", MedGadget, Sep. 18, 2009, 4 pgs.
"The Unique Force Sensor Ablation Catheter", www.endosense.com/site/product.htm, Mar. 14, 2007, 1 pg.
Barb, et al., "Versatile, High-Speed Force Transducer Using a Laser Diode Beam as an Optical Lever", Journal of Applied Physiology, vol. 88, No. 1, 2000, 308-314.
Barrett, et al., "Extrinsic Fabry-Perot Interometer for Measuring the Stiffness of Ailiary Bundles of Hair Cells", IEEE Transactions on Biomedical Engineering, vol. 46. No. 3, Mar. 1999, 331-339.
Rao, "Recent progress in applications of in-fibre Bragg grating sensors", Optics and Lasers in Engineering Elseiver JK, vol. 31, No. 4, Apr. 1999, 297-324.
International Search Report for International Application PCT/IB2017/050066 dated Mar. 16, 2017.

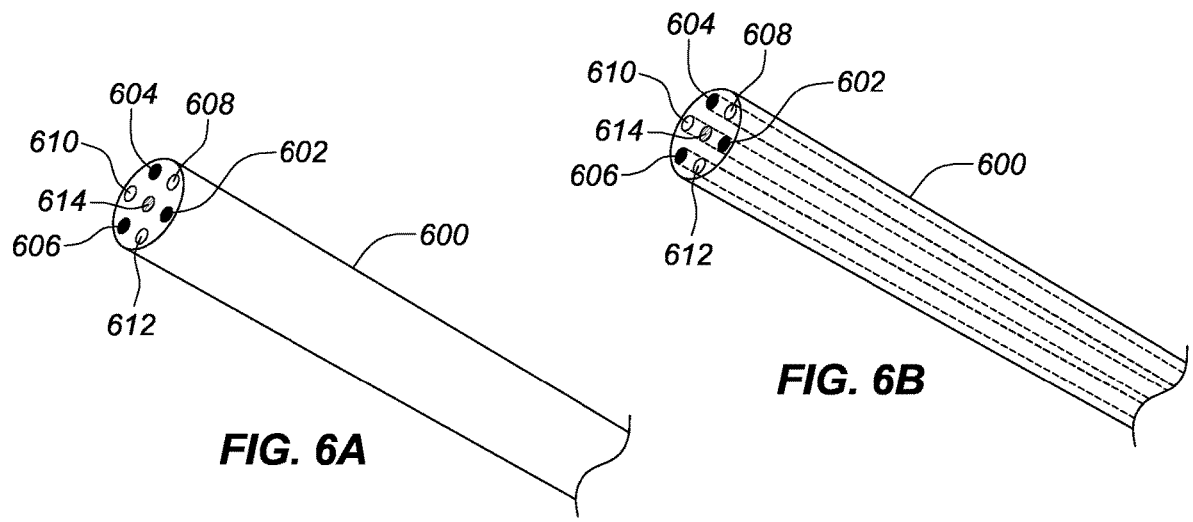
FIG. 6A
FIG. 6B
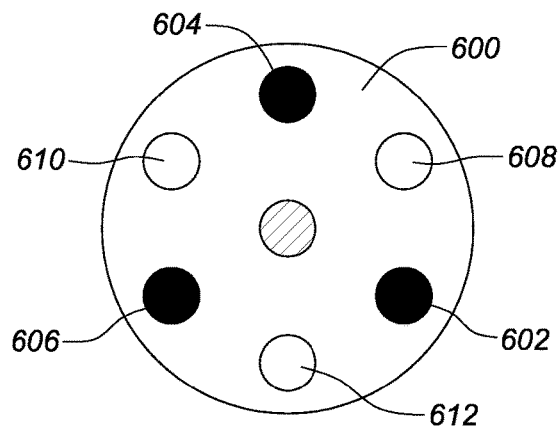
FIG. 6C
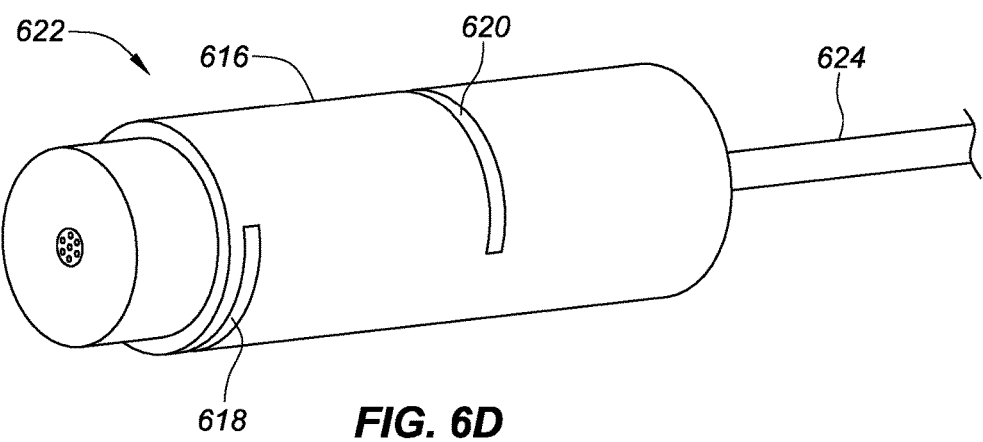
FIG. 6D

MEDICAL DEVICE WITH MULTI-CORE FIBER FOR OPTICAL SENSING

CROSS REFERENCE OF RELATED APPLICATION

This application is a continuation of U.S. patent application Ser. No. 15/400,655, filed Jan. 6, 2017, which claims priority to U.S. Provisional Application Ser. No. 62/275,877, filed Jan. 7, 2016, both of which are incorporated by reference in their entirety.

BACKGROUND a. Field

This disclosure relates to medical devices, and particularly to interventional and/or surgical catheters and other elongate medical devices capable of being visualized within a body as well as providing responsive feedback concerning tissue contact with a distal portion of the medical device.

b. Background

Within a cardiac cycle, the human heart experiences electrical impulses traversing from the sinus node to the ventricles. Cardiac contraction is driven by a cycle of polarization and depolarization as electrical currents spread across the heart. In healthy hearts, the heart will experience an orderly progression of depolarization waves called sinus rhythm. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, including death.

Catheters are used in a variety of diagnostic and/or therapeutic medical procedures to diagnose and correct conditions such as atrial arrhythmia, including for example, ectopic atrial tachycardia, atrial fibrillation, and atrial flutter. Typically, in atrial fibrillation therapies, a catheter is manipulated through a patient's vasculature to the patient's heart carrying one or more electrodes which may be used for mapping, ablation, diagnosis, or other treatment. Where an ablation therapy is desired to alleviate symptoms of atrial fibrillation, the ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radio-frequency (RF), cryoablation, laser, chemical, and high-intensity focused ultrasound. Ablation therapies often require precise positioning of the ablation catheter, as well as precise pressure exertion for optimal ablative-energy transfer into the targeted myocardial tissue. Excess force between the ablation catheter tip and the targeted myocardial tissue may result in excessive ablation which may permanently damage the cardiac muscle and/or surrounding nerves. When contact force between the ablation catheter tip and the targeted myocardial tissue is below a target force, the efficacy of the ablation therapy may be reduced, or entirely negated.

Ablation therapies are often delivered by making a number of individual ablations in a controlled fashion in order to form a lesion line. To improve conformity of the individual ablations along the lesion line, it is desirable to precisely control the position at which the individual ablations are conducted, the ablation period, and the contact force between the ablation catheter tip and the targeted tissue. All of these factors affect the conformity of the resulting lesion line. Catheter localization systems, in conjunction with mapping systems, have vastly improved a clinician's ability to precisely position the ablation catheter tip for an ablation and determine the efficacy of a treatment. Similarly, ablation controller circuitry has improved the consistency of individual ablation therapies. There are devices that attempt to measure the force exerted between myocardial tissue and the ablation catheter tip. Existing designs utilize ablation catheter tips with deformable bodies which deform in response to a force being exerted on the ablation catheter tip. Sensors (e.g., magnetic, optical, etc.) are used to approximate the deformation of the deformable body and to output a signal to controller circuitry that associates the deformation with a force exerted by the ablation catheter tip. However, existing deformable body designs suffer from both complexity and cost, primarily related to acquisition and delivery of the measurement signal to the proximal end of the catheter.

The foregoing discussion is intended only to illustrate the present field and should not be taken as a disavowal of claim scope.

BRIEF SUMMARY

The present disclosure relates to medical devices, and particularly to interventional and/or surgical catheters and other elongate medical devices capable of being visualized within a body as well as providing responsive feedback concerning tissue contact with a distal portion of the medical device.

In one embodiment, a medical device flexing structure assembly can comprise a multi-core fiber comprising a plurality of cores, and a flexing structure comprising at least one slot. Each of the plurality of cores can comprise a fiber Bragg grating, and the flexing structure can be configured to bend in response to a force imparted on the flexing structure.

In another embodiment, a surgical catheter can comprise a catheter tip assembly coupled to a distal end of a catheter body. The catheter tip assembly can comprise a catheter tip, a flexing structure, and a multi-core fiber, and the multi-core fiber can comprise a plurality of cores. A proximal end of the catheter tip can be coupled to a distal end of the flexing structure, a distal portion of the multi-core fiber passes through an interior portion of the flexing structure, and the flexing structure is configured to bend in response to a force imparted on the catheter tip.

In yet another embodiment, a surgical catheter can comprise a catheter tip assembly coupled to a distal end of a catheter body. The catheter tip assembly can comprise an electrode, a ferrule, and a multi-core fiber, and the multi-core fiber can comprise a plurality of cores. A proximal end of the electrode can be coupled to a distal end of the ferrule, a distal portion of the multi-core fiber passes through an interior portion of the flexure, and the electrode is configured to bend in response to a force imparted on the catheter tip.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIGS. 6A and 6B are an isometric views of another embodiment of a multi-core fiber.

FIG. 6C is an end view of the multi-core fiber of FIGS. 6A and 6B.

FIG. 6D is an isometric view of one embodiment a flexing structure comprising a multi-core fiber.

DETAILED DESCRIPTION

In the following description, reference is made to the accompanying drawings that depict representative examples. It is to be understood that other embodiments and implementations may be utilized, as structural and/or operational changes may be made without departing from the scope of the disclosure. Like reference numbers are used throughout the disclosure where appropriate.

The disclosure is generally directed to medical devices. Devices and techniques are disclosed relating to interventional and/or surgical catheters, introducers, and other elongate medical devices capable of being visualized within a body, as well as being capable of providing responsive feedback concerning tissue contact with a distal portion of the medical device.

In one embodiment, a catheter or other elongate medical device is equipped with distal force sensing capabilities and elongate body shape sensing capabilities. In one embodiment, the distal force sensing and elongate body shape sensing capabilities are implemented with optical sensing technology. Such optical sensing technologies may involve different optical sensing technologies, such as, for example, fiber Bragg grating (FBG) shape sensing and optical interferometer distal force sensing. However, embodiments described herein using optical conduits (e.g., optical fibers, fiber cores, etc.) may utilize any optical technologies that transmit light via such optical conduits for use in the force and shape sensing mechanisms, whether the implemented force and shape sensing technologies are the same or dissimilar.

Representative embodiments described herein also involve implementing a multi-core fiber(s) to provide the optical conduits through some or all of the catheter or other elongate body.

Figure 1:
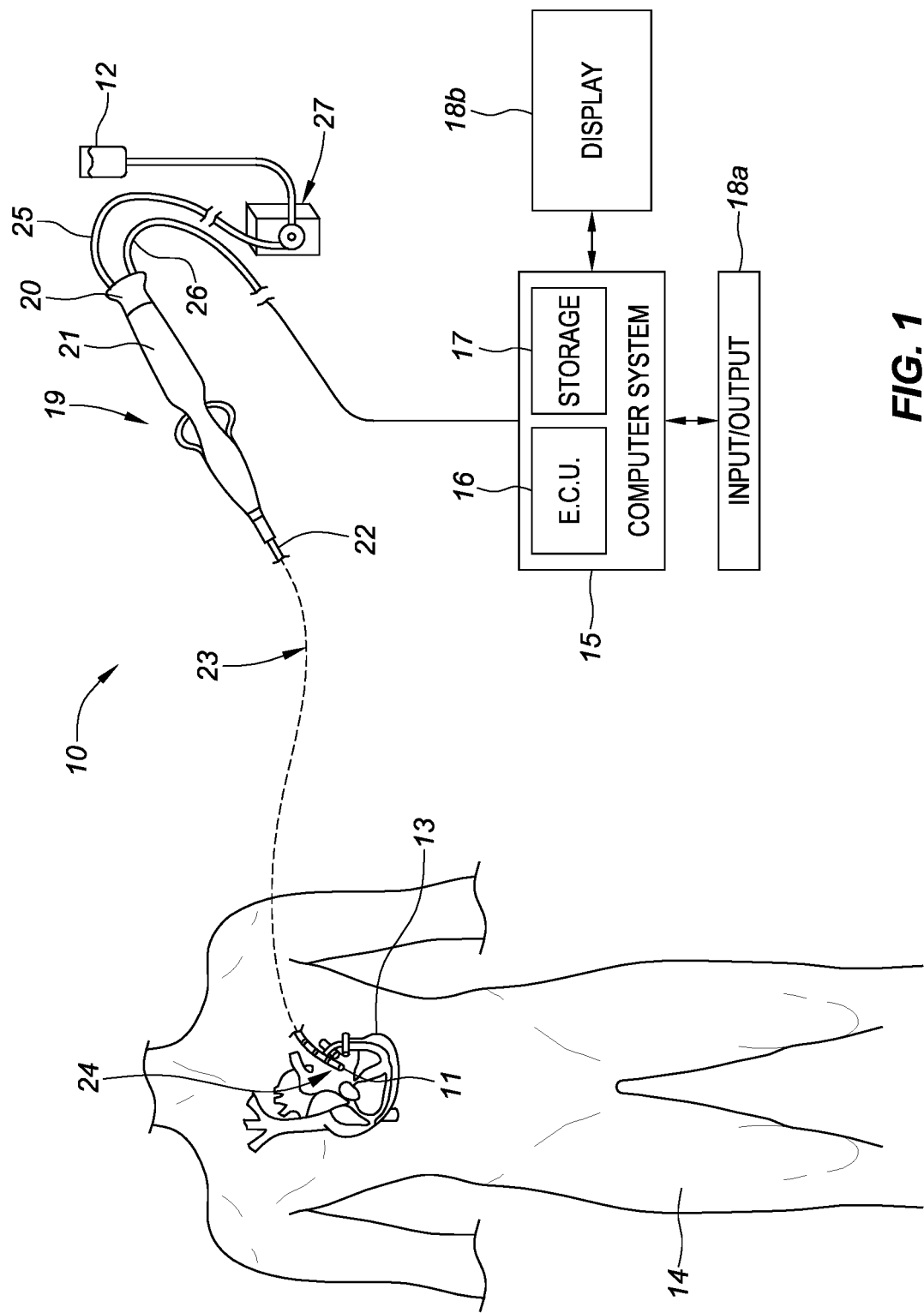
FIG. 1 is a diagrammatic view of a system that can be used to perform an interventional medical procedure.

FIG. 1 illustrates a representative system 10 that may be used in an interventional medical procedure on a body 14. While the description herein may be described in terms of a particular representative medical procedure and/or body 14 organ(s), it should be recognized that the principals described herein are equally applicable to other procedures and body organs. For example, while portions of the description may be described in terms of cardiac procedures and/or in terms of endocardial procedures involving the human heart, the principals described herein are equally applicable to other interventional procedures, such as epicardial procedures, renal denervation or other procedures involving the kidneys, vascular procedures, and the like.

Referring to FIG. 1, the system 10 includes a medical device, such as a catheter 19, introducer, or other interventional or surgical device where at least a portion of the device is placed within the body 14. The representative catheter 19 includes a catheter electrode assembly 11 shown within the cardiac space within the body 14, where the electrode assembly 11 is included as part of the catheter 19 or other medical device and may be used, for example, for diagnosis, visualization, and/or treatment of tissue 13 (such as cardiac or other tissue) in the body 14. For example, the electrode assembly 11 may be used for ablation therapy of tissue 13 and/or mapping purposes in a patient's body 14.

FIG. 1 further shows various representative sub-systems included in the overall system 10. The system 10 may include a main computing system 15, which may include a processing system, depicted in FIG. 1 as an electronic control unit (E.C.U.) 16 which represents any individual or distributed processing unit. The computing system 15 may also include data storage 17, e.g., memory and/or other storage. The computer system 15 may further include conventional interface components, such as various user input/output mechanisms 18a and a display(s) 18b, among other components. Information obtained and/or provided by the electrode assembly 11 may be processed by the computer system 15, and may provide data to the clinician via the input/output mechanisms 18a and/or the display 18b, or in other ways as described herein or known in the art.

In the illustrative embodiment, the catheter 19 may include one or more cable connectors or other interface 20, a handle 21, an elongate (e.g., tubular) body or shaft 22 having a proximal portion 23 and a distal portion 24. The distal portion 24 does not represent any particular length, but rather distinguishes some usable portion of the shaft 22 within the body 14 from a remainder of the shaft 22 that ultimately couples to the handle 21 or other control mechanism (e.g., robotic controller). The catheter 19 may also include other conventional components not illustrated herein such as a temperature sensor(s), additional electrodes, corresponding conductors or leads, etc. The connector 20 may provide mechanical, fluid, optical and/or electrical connections for cables, such as cables 25, 26. In the case of an irrigated catheter, a cable(s) 25 may extend from a fluid reservoir 12 and fluid pump 27, and the computer system 15. The connector 20 may comprise conventional components known in the art and, as shown in the illustrated embodiment, may be disposed at the proximal end of the catheter 19.

In the case of a manually controlled catheter, a handle 21 provides a portion for a user to grasp or hold the catheter 19, and may further provide a mechanism for steering or guiding the shaft 22 within the patient's body 14. For example, the handle 21 may include a mechanism configured to change the tension on a pull-wire(s) extending through the catheter 19 to the distal portion 24 of the shaft 22, or may include some other mechanism to steer the shaft 22. The handle 21 may be conventional in the art, and it will be understood that the configuration of the handle 21 may vary. In an embodiment, the handle 21 may be configured to provide visual, auditory, tactile and/or other feedback to a user based on information received from the electrode assembly 11 or elsewhere along the shaft 22. For example, if contact to tissue 13 is made by the electrode assembly 11, any one or more of the handle 21, computing system 15, I/O 18a and/or display 18b may include graphical output, light-emitting-diodes or other visual indicators, tone generator, a vibrating mechanical transducer, and/or other indicator(s), the outputs of which could vary in proportion to the signal sensed at the electrode assembly.

The system 10 of FIG. 1 is merely an exemplary system described to provide a representative context in which the principals described herein may be utilized. Catheter-based diagnostic and treatment systems have been widely used for exploration and treatment of various organs or vessels. Such catheters are typically introduced through a vessel leading to the cavity of the organ to be explored or treated, or alternatively may be introduced in other ways such as directly through an incision made in the wall of the organ. This treatment avoids the trauma and extended recuperation times typically associated with open surgical procedures. For purposes of illustration, descriptions below may be described in representative context of a cardiac ablation procedure using an ablation catheter.

In order to provide effective diagnosis or therapy, the areas to be treated may first be mapped. Such mapping may be performed, for example, when it is desired to selectively ablate current pathways within the heart to treat atrial fibrillation or other electrical cardiac conduction issues. Often, the mapping procedure is complicated by difficulties in locating the zone(s) to be treated due to periodic movement of the heart throughout the cardiac cycle. Current systems rely on manual feedback of the catheter and/or impedance measurements to determine when the catheter is properly positioned in the vessel or organ. Better procedure efficacy may be obtained by measuring contact forces with the vessel or organ wall or detecting contact forces applied by the catheter against the organ or vessel wall that may modify the true wall location. For radio frequency (RF) ablation treatment, sustained contact force is beneficial as less contact force may result in poor ablation, and too much force can result in safety issues such as perforating the organ. Thus, it is desirable to provide apparatuses and methods for detecting and monitoring contact forces between a catheter and the wall of the organ or vessel to permit faster and more accurate diagnostic and treatment.

As described in greater detail below, one such contact force technology involves optical sensors, such as sensors based on fiber Bragg grating. A fiber Bragg grating (FBG) is a desirable sensor for measuring the force for numerous reasons, such as it does not interfere with electronics and is compact in size. The FBG is a type of distributed Bragg reflector constructed in a segment of optical fiber that reflects particular wavelengths of light and transmits all others. This is achieved by creating a periodic variation in the refractive index of the fiber core thorough two light beams interfering. All wavelength lights have weak reflections at refractive index fringes, but only those wavelengths with phase matching condition will reflect back due to resonance effect and all other wavelength will transmit through the fiber.

For a grating with a period of $\Lambda$ and fiber core effective index $n_{\mathit{eff}}$, the Bragg wavelength $\lambda_B$ is determined by the resonance condition as $$\lambda_B = 2n_{\mathit{eff}}\Lambda \qquad (1)$$

When a strain is applied to the fiber grating or ambient temperature changes, both the grating period and the fiber effective index will change accordingly, and hence the Bragg wavelength will shift to blue or red wavelength sides. By measuring the shift of the Bragg wavelength, the FBGs can be used for force and temperature sensing. One advantage derives from the absolute nature of the information-encoding in measuring the wavelength shift, which renders the sensor independent from fluctuating light power or connector losses. With an applied strain $\varepsilon$ and the ambient temperature change dT, the shift of the Bragg wavelength is obtained by differential Eq. (1) as $$\frac{d\lambda}{\lambda_B} = (1 - \rho_e)\varepsilon + (\xi + \alpha)dT \qquad (2)$$

where $$\rho_e = -\frac{1}{n_{\mathit{eff}}} \frac{\partial n_{\mathit{eff}}}{\partial \varepsilon}$$

is the photo-elastic constant; $\rho_e = 0.22$ for pure silica glass.

$$\alpha = \frac{1}{\Lambda}\frac{\partial \Lambda}{\partial T} \sim 0.5 \times 10^{-6}$$

is the coefficient of linear expansion, $$\xi = \frac{1}{n_{\mathit{eff}}}\frac{\partial n_{\mathit{eff}}}{\partial T} \sim 7 \times 10^6$$

is the thermo-optic coefficient, and dT is the temperature change. For a grating at 1550 nm wavelength, the wavelength shifts are typically of order ~1 pm/µε for strain, and 10 pm/° C. for temperature.

The Yong's modules E is defined as $$E = \frac{\text{stress}}{\text{strain}} = \frac{F/A_0}{\Delta L / L_0} \qquad (3)$$

Where, F is the force, $A_0$ is the area of the fiber cross section, $L_0$ is the fiber length and $\Delta L$ is stressed length due to the applied force. The force is thus derived from Eq. (3) as $$F = EA_0\varepsilon \qquad (4)$$

where $\varepsilon = \Delta L / L_0$ is the stain. For a single mode fiber with a diameter of 125 um, the Yong's modulus of the glass material is $70 \times 10^9$ N/m², then the force with respect to the fiber strain is obtained as $$F = 859\varepsilon(N) \qquad (5)$$

When the ambient temperature remains unchanged dT=0, for a pure glass $\rho_e$=0.22, submit Eq. (5) into Eq. (2), the applied force with respect to the shift of the Bragg wavelength is obtained as $$F \approx 1101 d\lambda/\lambda_B \quad (6)$$

For a resolution of 0.01 nm Bragg wavelength shift in 1550 nm wavelength band, the force resolution is given by Eq. (6) as 0.7 gram.

Submit Eq. (4) into Eq. (2), the shift of Bragg wavelength with respect to the applied force and temperature change is expressed as $$\frac{\Delta\lambda}{\lambda_B} = (1-\rho_e)\frac{F}{EA_0} + (\xi+\alpha)\Delta T \quad (7)$$

Where $\Delta\lambda$ is the shift of Bragg wavelength, $\Delta T$ is the temperature change, F is the applied force, E is the Yong's module, $A_0$ is the area of fiber cross section, $\rho_e$ is the photo-elastic constant, $\alpha$ is the coefficient of linear expansion, $\xi$ is the thermo-optic coefficient.

To sense three-dimensional (3D) vector force and temperature, four independent sensors may be used in one embodiment. Four single FBGs can be used for the sensing, but ample space may be needed to mount the four FBGs. Additionally, all four FBGs may also involve separate calibration due to mechanical assembly, which limits the FBGs for sensing applications, especially in catheter applications as the size of the catheter tip may be only a few millimeters. The present disclosure describes a multi-core fiber comprising multiple core fibers that run the length of the fiber. The multi-core fiber can assist in limiting the cross-sectional space required within a catheter body for a plurality of independent channels as described herein.

In accordance with one embodiment, when an FBG is inscribed on a multi-core fiber (MCFBG), e.g. four core fibers, four FBGs on four fiber cores can act as four sensors, but the overall size still corresponds to that of the single mode fiber. There can be no separate calibration issue, as all four FBGs are in the same fiber. If all cores are constructed substantially the same, the temperature change will correspondingly shift all four Bragg wavelengths, while only the force in the fiber axis direction will shift four Bragg wavelengths in the same mount. When force is applied to the MCFBGs with an angle, the fiber will be bent, and thus four FBGs will experience different compression and tension respectively while the Bragg wavelengths will shift to either short or long wavelengths depending on the force amplitude and its direction. In one embodiment, the end surface of MCFBGs is melted or otherwise amalgamated (e.g., into a ball) to minimize the reflection.

Figure 2A:
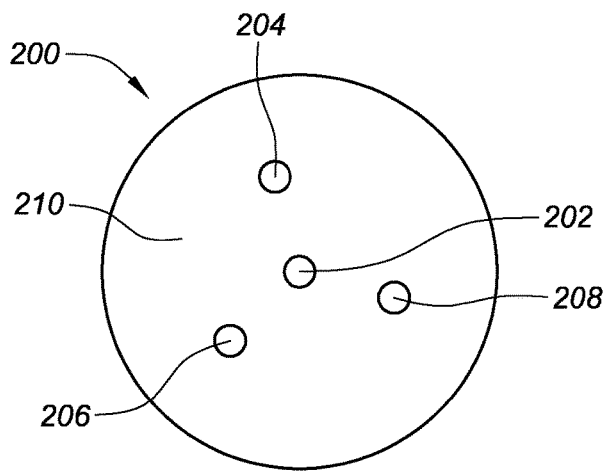
FIG. 2A is an end view of one embodiment of a multi-core fiber.
Figure 2B:
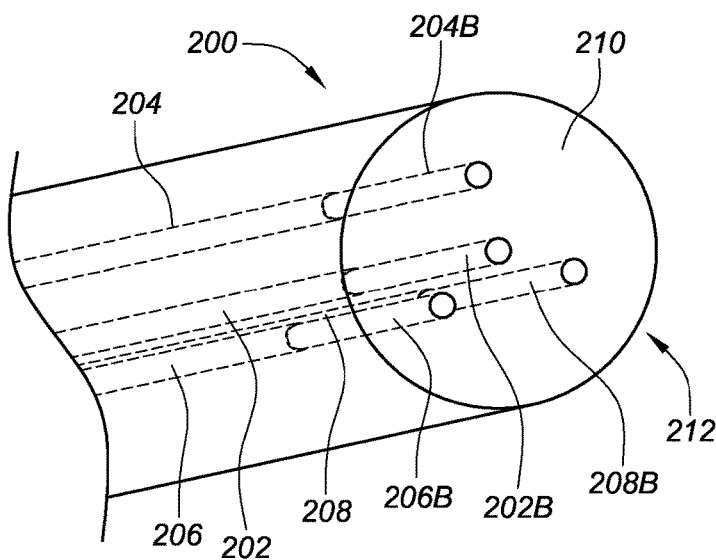
FIG. 2B is an isometric view of an end of the multi-core fiber of FIG. 2A.

FIGS. 2A and 2B illustrate a representative multi-core fiber (MCFBG) 200 in accordance with an embodiment In the illustrated embodiment the MCFBG 200 can comprise multiple cores The multiple cores can comprise an MCFBG body 210, a distal end 212, a central core 202, a second core 204, a third core 206, and a fourth core 208. The MCFBG body 210 can comprise glass or plastic materials. These materials can comprise various configurations as would be known to one of skill in the art. The MCFBG can comprise silica among other materials. The multiple cores can provide at least optical/light conduits for sensing force impacting the distal portion of a catheter. The core diameters and dopants of the multi-core fiber can be the same, or different. In one embodiment, a central core 202 can achieve different refractive effective index, temperature and strain coefficient to improve the force and temperature sensitivity. In another embodiment, the force and temperature sensitivity can be improved when the fiber cladding is designed with a structure of small holes or FBGs on multi-core crystal fibers. In the illustrated embodiment, the central core 202 may be used to sense temperature changes by way of an optical sensor (e.g., FBG) at distal core section 202B, which allows temperature compensation for the remaining off-axis cores 204, 206, 208 that transmit light to the respective force sensing (e.g., FBG) sections. In one embodiment, the MCFBG can be disposed along a central axis of a catheter and the central core can be used to sense temperature changes by way of an optical sensor. In other embodiments, one or more of the other cores present in the MCFBG can be used to sense temperature changes by way of an optical sensor. Each of the off-axis cores can comprise a distal section. In the illustrated embodiment, the MCFBG 200 can further comprise a second distal section 204B, a third distal section 206B, and a fourth distal section 208B.

Figure 2C:
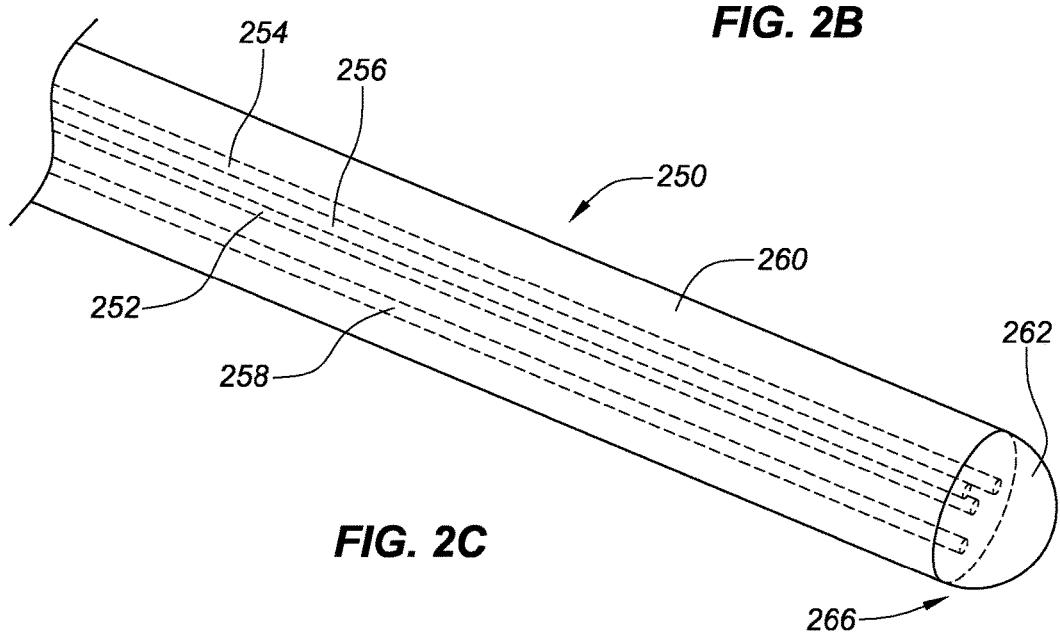
FIG. 2C is an isometric view of an end of another embodiment of a multi-core fiber.

FIG. 2C illustrates another embodiment of an MCFBG 250. In the illustrated embodiment, the MCFBG 250 can comprise an MCFBG body 260, a distal end 266, a central core 252, a second core 254, a third core 256, and a fourth core 258. In the illustrated embodiment, the distal end 266 of the MCFBG 250 can be melted into a distal cap 262. The distal cap can comprise a ball-like shape. The ball-like shape can be used to minimize reflection from light traveling to the distal end 266, as depicted in FIG. 2C. In the illustrated embodiment, the distal cap 262 can comprise the same material as the MCFBG body 260. In other embodiments, the cap can comprise a portion of the MCFBG body that has been crushed. By crushing a distal end of the MCFBG, as with melting, a distal cap can be formed that minimize reflection from light traveling to the distal end of the MCFBG. In other embodiments, the distal cap can comprise other materials placed on the distal end of the MCFBG. In various embodiments the distal cap can comprise an adhesive or other material that can be formed in a desired shape and/or comprise a desired reflective property.

As seen above, since Eq. (7) is a linear equation, the force and the temperature change will linearly shift all four FBG wavelengths and the force and temperature are then expressed as $$F_i = \sum_{j=1}^{4} A_{ij} \Delta\lambda_j \quad (8)$$

$A_{ij}$, i,j=1,2,3,4 represent the sixteen coefficients related to the mechanical assembly and material strengths that can be determined by experiments; $\Delta\lambda_i$ i=1,2,3,4 indicate the four shifts of Bragg wavelengths, respectively; $F_i$, i=1,2,3 represents three components of force, $F_4$ is the temperature change. The amplitude and the direction angles of the force are expressed as $$\begin{cases} F = \sqrt{F_1^2 + F_2^2 + F_3^2} \\ \theta = \cos^{-1}(F_1/F) \\ \gamma = \cos^{-1}(F_2/F) \\ \Delta T = F_4 \end{cases} \quad (9)$$

where $F_1$, $F_2$ and $F_3$ are the three components of the force, $\theta$ and $\gamma$ are the direction angles of the force, respectively. When a computer controlled optical switch makes a scan from channel 1 to 4 acquiring the Bragg wavelength shifts, the applied force and temperature change are achieved from Eq. (9).

Figure 3:
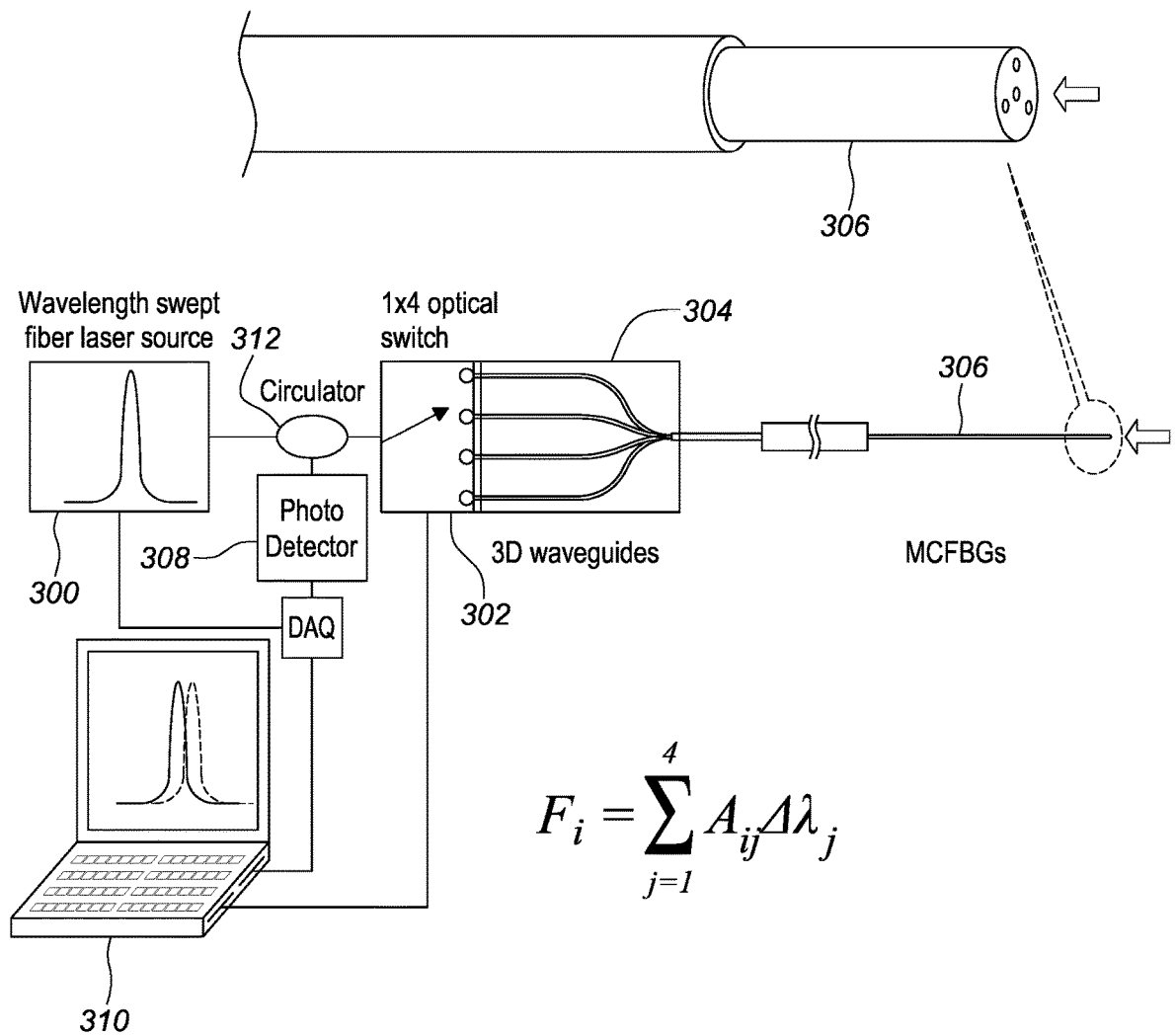
FIG. 3 is a diagrammatic view of one embodiment of a force sensing system.

FIG. 3 is a diagram of a representative force sensing system utilizing a wavelength swept fiber laser source 300, an optical switch 302, a 3D waveguide 304, a computer 310, a photo detector 308, a circulator 312, and a multi-core fiber Bragg gratings 306. In one embodiment, the computer 310 can comprise a microprocessor. The computer can control the wavelength swept fiber laser source 300 to emit an electromagnetic source or other signal. In the illustrated embodiment, the wavelength swept fiber laser source 300 can transmit the source signal to the circulator 312. The source signal can then pass through the optical switch 302, pass through the 3D waveguide 304, and travel from a proximal end to a more distal portion of the multi-core fiber Bragg gratings 306. A portion of the signal can then be reflected and/or refracted towards the proximal end of the multi-core fiber Bragg gratings 306, through the circulator 312 and to the photo detector 308. In one embodiment, the photo detector 308 can send a signal to the computer 310. The computer can then process the signal to determine a degree of deflection enacted on a distal end of the multi-core fiber Bragg gratings 306 as described herein. In another embodiment, the signal returning from the multi-core fiber Bragg gratings can be directed to a sensor coupled to or part of the computer. While the multi-core fiber Bragg gratings is illustrated separately in the illustrated embodiment, the multi-core fiber Bragg gratings can be placed within a medical device or other object as described throughout this application.

Figure 4:
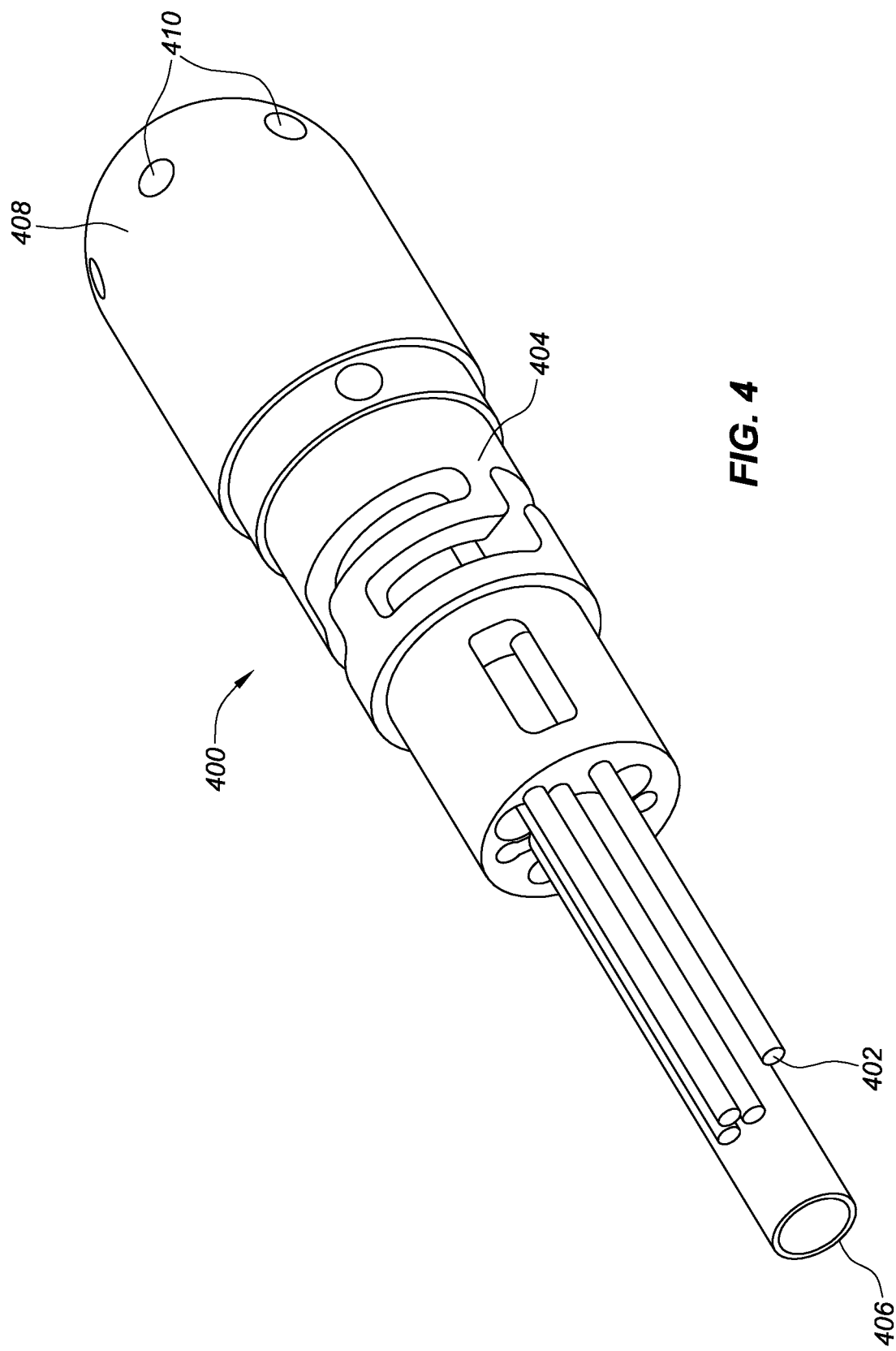
FIG. 4 is an isometric view of one embodiment of a catheter tip comprising a multi-core fiber.

FIG. 4 illustrates an isometric view of a representative catheter tip assembly 400 comprising a tip electrode 408, a plurality of irrigation holes 410, an irrigation tube 406, a multi-core FBG 402 and a force coupler 404. The tip electrode 408 can be coupled to the force coupler 404. In some embodiments, the force coupler can comprise a deformable body. Further the multi-core FBG 402 can be coupled to an interior portion of the force coupler 404. When a force is enacted upon the tip electrode 408, the force can be transferred to the force coupler 404 and the multi-core FBG 402 can deform in response to movement of the force coupler 404. When the multi-core FBG 402 deforms, signals interact with the FBG present within the multi-core FBG and the change in signal can be used to determine the force acting upon the tip electrode.

Figure 5A:
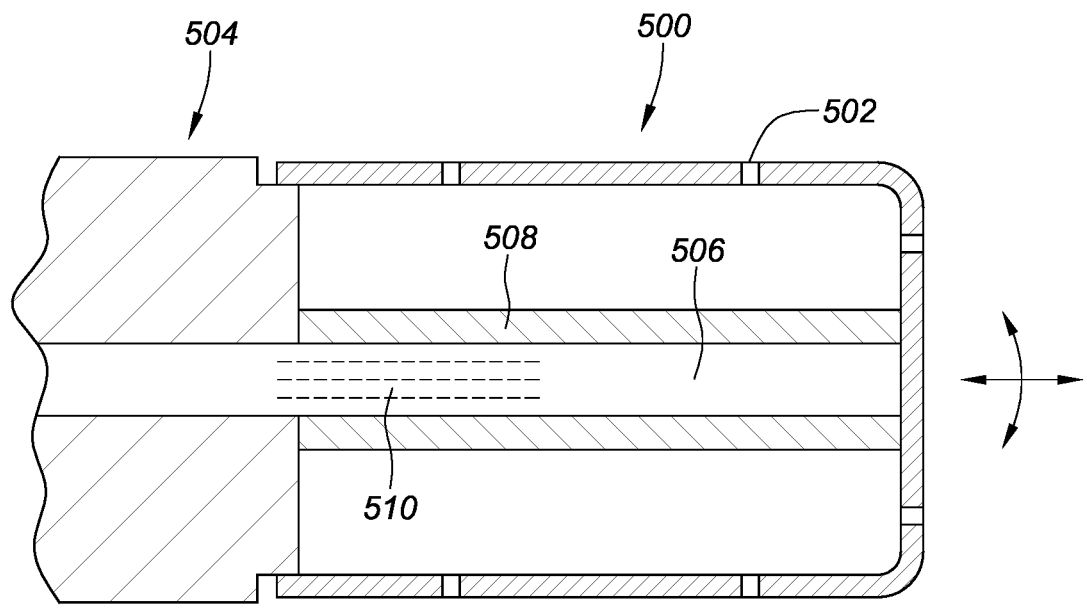
FIGS. 5A and 5B are cross-sectional views of other embodiments of a catheter tip comprising a multi-core fiber.

FIG. 5A shows a cross-sectional view of another representative catheter tip assembly 500. The catheter tip assembly can comprise an electrode 502, a fiber 506, an encasement tube 508, and a ferrule 504. The electrode 502 can swivel angularly or be compressed axially. In one embodiment, the ferrule 504 can be coupled to a proximal end of the electrode 502. In another embodiment, the ferrule 504 can be coupled to the fiber 506 and can be located proximate a proximal end of the electrode 502. An outer surface of the fiber 506 can be surrounded by the encasement tube 508. In one embodiment, a distal end of the fiber 506 and the encasement tube 508 can be coupled to a distal portion of the electrode 502. In another embodiment, the distal end of the fiber and the encasement tube can be free floating within the electrode. In another embodiment, the fiber 506 and the bonded encasement tube 508 can act as the primary spring. The fiber 506 can comprise a plurality of cores 510. The plurality of cores can run from a proximal end of the fiber to a distal end of the fiber. In the illustrated embodiment, the encased fiber 506 can have a length/diameter ratio that is short enough that buckling is precluded under axial compression but long enough to provide bending sensitivity. In various embodiments, this ratio may be, for example, in the 3:1 to 10:1 range, or other ranges that would be desirable and known to one of ordinary skill in the art. In the illustrated embodiment, the catheter tip assembly can comprise a non-irrigated electrode. In other embodiments, the electrode can be further configured to couple to an irrigation tube and direct an irrigant to an area exterior the electrode.

Figure 5B:
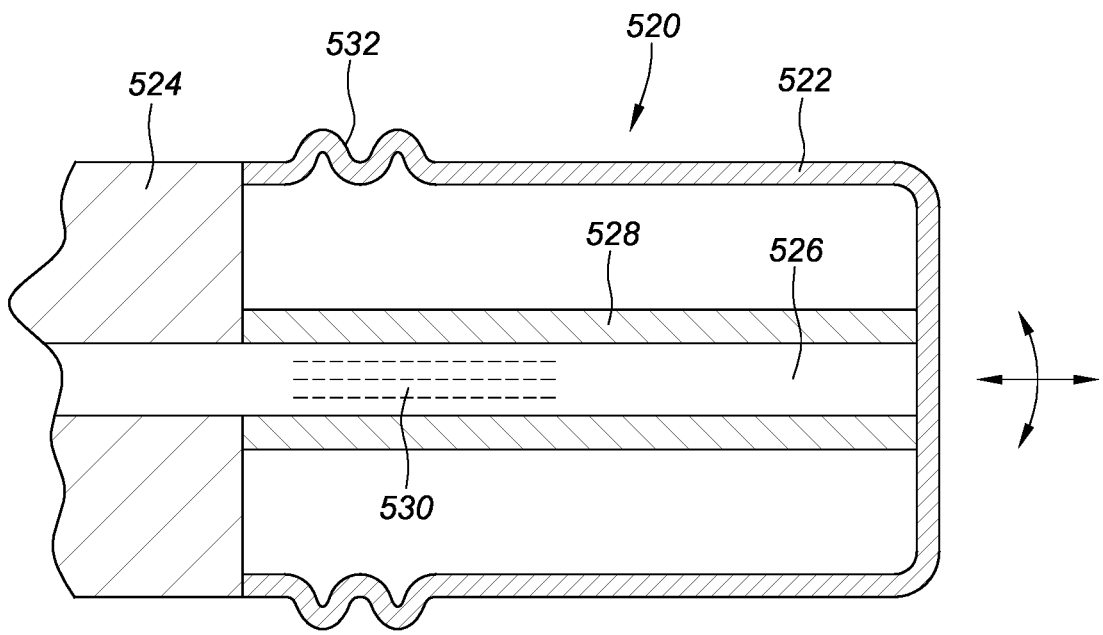

FIG. 5B shows another embodiment of a catheter tip assembly 520. The catheter tip assembly 520 can comprise an electrode 522, a ferrule 524, a fiber 526, and an encasement 528. The electrode 522 can comprise at least one deformation mechanism 532. In various embodiments the deformation mechanism 532 can comprise corrugations, laser slots, or other mechanisms of deformation which can allow the electrode 522 to deform with a spring constant. In the illustrated embodiment, the overall net spring used in calculations is a mechanically parallel combination of a spring action for the electrode 522 and from a mechanically parallel spring action provided by the fiber 526 with the encasement 528. An outer surface of the fiber 526 can be surrounded by the encasement tube 528. In one embodiment, a distal end of the fiber 526 and the encasement tube 528 can be coupled to a distal portion of the electrode 522. In another embodiment, the distal end of the fiber and the encasement tube can be free floating within the electrode.

Figure 5C:
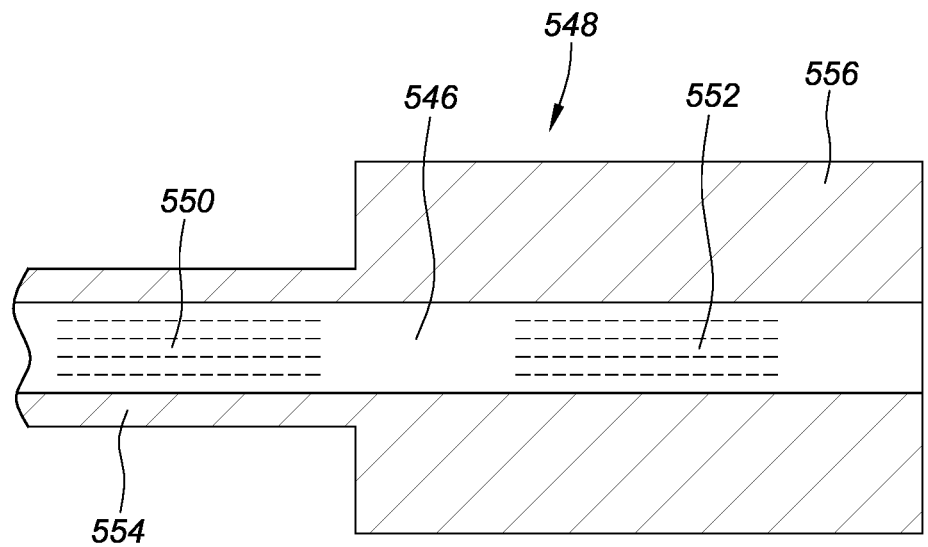
FIG. 5C is a cross sectional view of one embodiment of an encasement member.

FIG. 5C depicts an embodiment of an encasement member 548 and its encased fiber 546. The encasement member 548 can comprise a proximal wall 554 and a distal wall 556. In the illustrated embodiment, the proximal wall 554 of the encasement member 548 can comprise a thinner wall that that of the distal wall 556. The fiber 546 can comprise a first set of gratings 550 and a second set of gratings 552. In the illustrated embodiment, the first set of gratings 550 can be proximal of the second set of gratings 552. Further, the first set of gratings 552 can be adjacent or proximate the proximal wall 554 of the encasement member 548. In other embodiments, an outer surface of the fiber 546 at the first set of gratings 550 can be surrounded by the proximal wall 554. The second set of gratings can be adjacent or proximate the distal wall 556 of the encasement member 548. In other embodiments, an outer surface of the fiber 546 at the second set of gratings 552 can be surrounded by the distal wall 556. In the illustrated embodiment, the multi-core fiber 546 has multiple cores and multiple gratings. The first set of gratings 550 can used for bending and the second set of gratings 552 can used for axial compression and can be situated in the encasement member 548 at two different axial positions, one with a thin wall and the other with a relatively thicker wall. By using an encasement member with a wall of varying thickness, the sensitivities of bending and compression to be independently manipulated. The gratings 550 and 552 can be included in a common set of cores, or may be included in two separate sets of cores, or a combination thereof (e.g., where the central core for temperature compensation is shared, and separate sets of cores may be used for each of set of three force sensing cores). Further, while the illustrated embodiment discloses an encasement member with a thinner wall in a more proximate location and a thicker wall in a more distal location, other forms are also disclosed. In one embodiment, a thicker wall can be in a more proximate location and a thinner wall can be located in a more distal location. Further, in yet other embodiments, the wall can vary in thickness along its length. In other embodiments, the wall can slope from a first diameter to a second diameter. In one embodiment, the wall can slope from a thinner portion in a proximal location to a thicker portion in a more distal location. In another embodiment, the wall can slope from a thicker portion in a proximal location, to a thinner portion in a more distal location. Further, several step changes in thickness along a length of the encasement member are also contemplated.

Figure 5D:
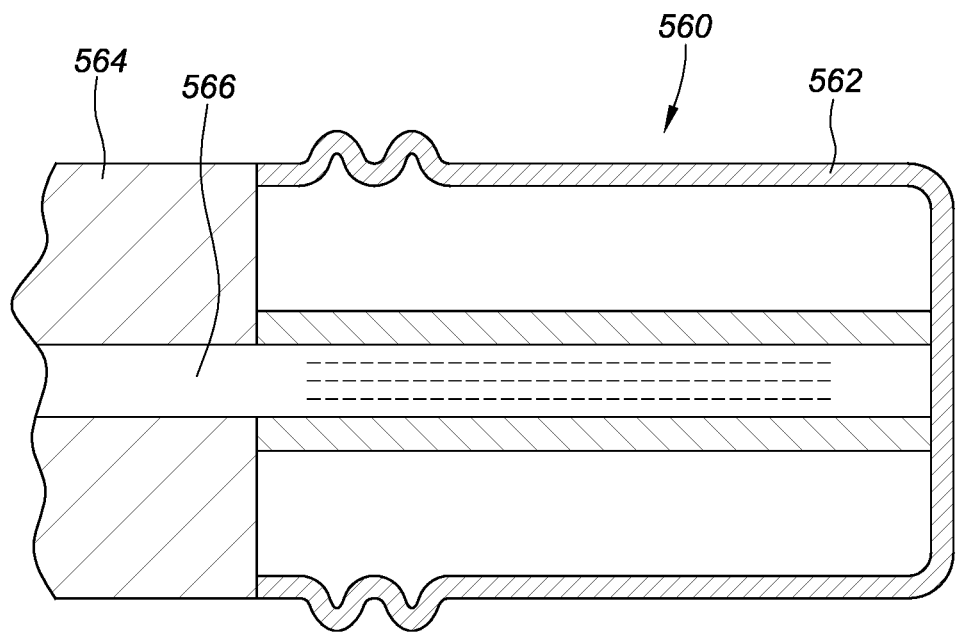
FIG. 5D is a cross-sectional view of another embodiment of a catheter tip comprising a multi-core fiber.

FIG. 5D depicts another embodiment of a catheter tip assembly 560. In the illustrated embodiment, the catheter tip assembly can comprise an electrode 562, a ferrule 564, and a multicore fiber 566. In one embodiment, a distal end of the multicore fiber 566 can be coupled to a distal portion of the electrode 562. In another embodiment, a distal end of the multicore fiber can be free floating within the electrode 562. In yet another embodiment, a distal end of the multicore fiber can be held in place against a distal portion of the electrode while not adhered or otherwise coupled to the electrode. The multicore fiber 566 can held in tension with little or no encasement member. The multicore fiber 566 can still sense both compression (tension reduction) and bending, where it has an appropriate length/diameter aspect ratio so that it is neither too floppy nor too stiff. The length/diameter aspect ratio can vary depending on the materials that are used to create the multicore fiber, and would be known to one of ordinary skill in the art.

Representative embodiments and variations using techniques described herein are now described for purposes of example and illustration. An embodiment of a medical catheter with a force-sensing capability may provide, for example, a distal diagnostic or therapeutic tip region which is to be juxtaposed against tissue with a force, an intermediate and more proximal extended flexible lumen, a most proximal control handle with which to manipulate the catheter lumen and tip region within a patient's body lumens or organs, a force sensor to sense one or both of a tip bending force and a tip axial force as the distal tip is contacted to a patient's tissue (e.g., cardiac tissue). In such an embodiment, the force sensor may comprise a combination of a force-displacement calibrated spring and two or more optical displacement sensors capable of reporting one or more deflections of the spring as force is applied to the tip, where the optical displacement sensors comprise two or more Bragg gratings written upon two or more cores of a multi-core optical fiber, and where the detected spring deflections permit the tip force to be computed and reported since the spring is calibrated for force versus deflection and deflection is known.

In further variations and alternatives, the optical displacement Bragg sensors may utilize wavelength scanning to determine displacement, where the wavelength scanning takes place in, for example, a console into which the catheter is connected, or in the handle of the catheter. Another option is for the multicore fiber to have at least two cores peripheral to the fiber outer diameter, where in a more particular example the multiple cores are angularly distributed about the fiber's central axis in an approximately equally spaced manner. Another option is for the multicore optical fiber to be optically connected to separate fibers using a 3D optical waveguides, which may further involve mounting an optical connector in or on the supporting or control console into which the catheter is plugged. In another embodiment, the calibrated spring includes a tubular multi-core fiber-encapsulating member whose spring stiffness includes the enclosed fiber. In another embodiment, the calibrated spring includes a separate spring which operates mechanically in parallel to any spring action provided by the fiber or its containment means, the overall net spring being the simultaneous combination of both springs in parallel. In yet another embodiment, the calibrated spring is separate from the fiber or its immediate encapsulation member, and the spring provides all of the calibrated spring action employed in force computation. Still another variation involves pre-stretching the fiber in tension or pre-compressing the fiber in compression during manufacture whether or not the fiber is itself encapsulated. Another variation includes a temperature measurement sensor to correct a Bragg grating detected displacement for thermal expansion, where in an even more particular embodiment the temperature sensor is any one of i) a thermocouple, ii) a thermistor, iii) a Bragg grating whose thermal expansion can be deduced optically and thereby acts as a temperature sensor. Yet another variation of such a medical device positions two or more such Bragg gratings on two or more cores of the fiber, where the gratings have the same axial fiber positions. Alternatively, two or more such Bragg ratings are positioned on a single core of the fiber and have different axial fiber positions. In another example, two or more Bragg gratings on one or more cores may have substantially the same grating period, or may have different grating periods. In one embodiment of the catheter, a region of the multi-core fiber which contains one or more Bragg gratings retains the fiber cladding, where in another embodiment the fiber cladding is stripped therefrom. In yet another example, the spring allows for at least one of a combined tip bending and tip axial compression, tip bending only, or axial compression only, where in a more specific embodiment the two or more Bragg optical displacement sensors detect at least a component of one or more of a bending force and an axial force. In yet another example, the net force or force component is reported as a vector. Representative variations of the catheter tip include the catheter tip being capable of ablating tissue using a tissue heating or cooling method, the catheter tip being capable of electrically pacing tissue, and the catheter tip being capable of electrically sensing tissue electrical waveforms. In one embodiment, the force information may be displayed on a screen in any numeric, icon or vector form; as an indication that a minimum recommended force has been or has not been attained or has or has-not been maintained, or is used in combination with the time of exposure to the therapy such that a numeric product or index of force and time or force/time integral can be reported. In other variations, the multi-core fiber is designed to prevent fiber buckling. In one embodiment, one or more optical displacement sensors are at least one of (a) immersed in flowed irrigant (e.g., saline) and in direct contact with the irrigant/fluid; (b) immersed in flowed irrigant but isolated from the irrigant by an overlying, encapsulating or encasing member or coating; (c) immersed in flowed irrigant but thermally insulated or buffered from the irrigant by an overlying encapsulating or encasing member or coating having a preselected thermal conductivity; (d) immersed in air, a gas or a vacuum; (e) immersed in a deformable gel; (f) mounted in a groove or channel; (g) cast or molded into a surrounding polymeric containing member. In yet another embodiment, the multi-core optical fiber is also employed with additional Bragg gratings arranged in the intermediate flexible lumen such that the flexing shape of the lumen itself can also be tracked in addition to the tip force. In another embodiment, the multi-core fiber is also employed to perform optical lesion feedback or optical tissue analysis. In some embodiments, the temperature can be measured or frequently updated by holding the catheter in the blood without applied force. Another option involves using a particular core's FBG (e.g., the center FBG) as a reference as bending will not shift the center FBG wavelength. FBGs on three-core or more can be used to measure the force and temperature in one embodiment, where alternatives include: (a) doping one or more of the cores (e.g., the center core) with a different material than other cores to optimize the parameters to separate the Bragg wavelength shifts of the applied force from the temperature to improve the force and temperature sensitivities; (b) making one or more of the cores a different diameter (e.g., the center core) to optimize the parameters to improve the force and temperature sensitivities; (c) where the cladding of the multi-core fiber is optionally designed with holes to optimize the parameters to improve the force and temperature sensitivities; and (d) where FBGs on multi-core crystal fibers are used as a sensor to improve the force and temperature sensitivities.

In addition to providing force sensing functionality, other features may be included with such medical devices to provide further value for physicians during interventional or surgical medical procedures. For example, it would be beneficial to visually perceive relevant portions of the medical device that are otherwise veiled by the patient's body, such as a catheter shaft when introduced into the body and no longer directly visible. The present disclosure provides solutions to such challenges, by providing manners for tracking and mirroring the shape of some or all of the veiled portion of the medical device, such as some or all of the proximal portion and optionally some or substantially all of the distal portion of a catheter shaft during a medical procedure (e.g., during catheter-based diagnosis and/or treatment of tissue).

In one embodiment, both optical force sensing and optical shape sensing are provided. One such manner of providing optical force and shape sensing is described in U.S. Pat. No. 8,622,935, which is incorporated herein by reference in its entirety. Optical conduits, such as optical fiber, may be used to transmit light to optical force sensors that detect forces impacting the catheter tip due to varying contact pressures between the catheter tip and body tissue. Other optical conduits may be used to transmit light along a desired length of the catheter shaft equipped with optical sensors, in order to enable the real-time position of the sensed portion of the catheter shaft to be positionally tracked and rendered for simulation of the catheter shaft within the body.

The optical sensors used for sensing the force against tissue and for sensing the changing shape of the catheter may utilize different optical sensing technologies, or a common optical sensing technology. For example, in one embodiment, optical fibers may be equipped with fiber Bragg gratings or other optical sensors to determine deflection of a distal portion of a catheter, which is representative of a magnitude and direction of a force bearing upon the catheter tip when contacting tissue during a medical procedure. In the same or other optical fibers, fiber Bragg gratings or other optical sensors may also be employed along a length of the catheter shaft that is tracked in real time as the catheter moves and consequently changes shape during the medical procedure.

In embodiments further described below, the optical fibers used for both force sensing and shape sensing may be provided as multiple cores of a multi-core fiber. The multi-core fiber thus provides the light pathways and optical sensors for both force and shape sensing technologies.

One embodiment of a multi-core fiber accommodating both sensors for force sensing and shape sensing is depicted in FIG. 6A. FIG. 6A depicts an isometric view of a multi-core fiber 600. The multi-core fiber 600 can comprise a plurality of separate cores. In the illustrated embodiment, the multi-core fiber 600 can comprise three cores to provide optical conduits for three respective force sensors (not shown). The multi-core fiber 600 can comprise a first optical core 602, a second optical core 604, and a third optical core 606. The multi-core fiber 600 can further comprise a first shape sensing core 608, a second shape sensing core 610, and a third shape sensing core 612 to provide optical conduits for three respective shape sensing sensors (not shown). In the illustrated embodiment, a particular core located anywhere within the fiber, which in one embodiment is the central core 614, may be used to sense temperature changes by way of an optical sensor (e.g., FBG) at a distal core section. Sensing temperature with the central core 614 allows temperature compensation for the remaining off-axis cores 602-612. In other embodiments, four fibers can be used to derive a force component and a temperature. In one embodiment, a temperature peak and a normal peak can both be determined in the same gradient. In another embodiment, a temperature peak and a normal peak can both be determined in the same gradient and at the same magnitude. FIG. 6B depicts an isometric view of the multi-core fiber 600 of FIG. 6A, while also illustrating an extension of the cores 602-614 through the body of the multi-core fiber 600. In one embodiment, as illustrated above in FIG. 2C, a distal end of the multi-core fiber may be melted into a ball-like shape to minimize reflection. FIG. 6C depicts an end view of the multi-core fiber 600 illustrated in FIGS. 6A and 6B and depicts a representative arrangement of the multiple cores 602-612 of fiber 600 from a perspective perpendicular to a longitudinal axis of the fiber 600.

In one embodiment, only shape sensing cores are implemented, such that only the first shape sensing core 608, the second shape sensing core 610, and the third shape sensing core 612, and optionally an additional core 614 (centrally located or not centrally located), are provided in the multi-core fiber 600. For example, referring to FIG. 2B, the cores 204, 206, 208 may be configured as shape sensing cores having a plurality of fiber Bragg gratings along the fiber 200, and therefore along the catheter shaft in which the fiber is enclosed. One or more temperature sensors may be included in one or more cores of the fiber, such as was core 202 of FIG. 2B. In such an embodiment, only shape sensing is performed utilizing the multi-core fiber, versus both shape sensing and force sensing.

In another embodiment, both shape sensing and force sensing are implemented using common cores, such that each core includes both shape sensing and force sensing sensors. For example, the frequency of light can be different in a common core for each of the force and shape sensing gratings respectively, which allows differentiation of the resulting reflections at the sensor signal processing unit.

FIG. 6D depicts an isometric view of one embodiment of a flexing structure assembly 622. The flexing structure assembly 622 can comprise an exemplary multi-core fiber 624 implemented in a flexing structure 616. In one embodiment, the flexing structure assembly 622 can be positioned proximate a distal portion of a catheter shaft. In the illustrated embodiment, the flexing structure 616 accommodates distal flexing from which at least the force sensors may sense deflection due to force against a structure, such as cardiac tissue. In this embodiment, one or more slots, depicted as slots 618, 612, allow the flexing structure 616 to bend due to a force in response to contact with the tissue. For example, where one or more fiber Bragg grating force sensors are within three respective cores 602, 604, 606 (as seen in FIGS. 6A-6C), and within the flexing structure 616, the force sensors can identify deflection of the flexing structure 616 in response to varying degrees of contact with tissue. Such sensors based on fiber Bragg grating may be implemented as described herein, and/or as described in U.S. Pat. No. 8,182,433 assigned to the assignee of the instant application, which is incorporated herein by reference in its entirety. In other embodiments, the force sensors associated with the force sensing cores 602, 604, 606 (as seen in FIGS. 6A-6C) may utilize a different optical technology.

Figure 6E:
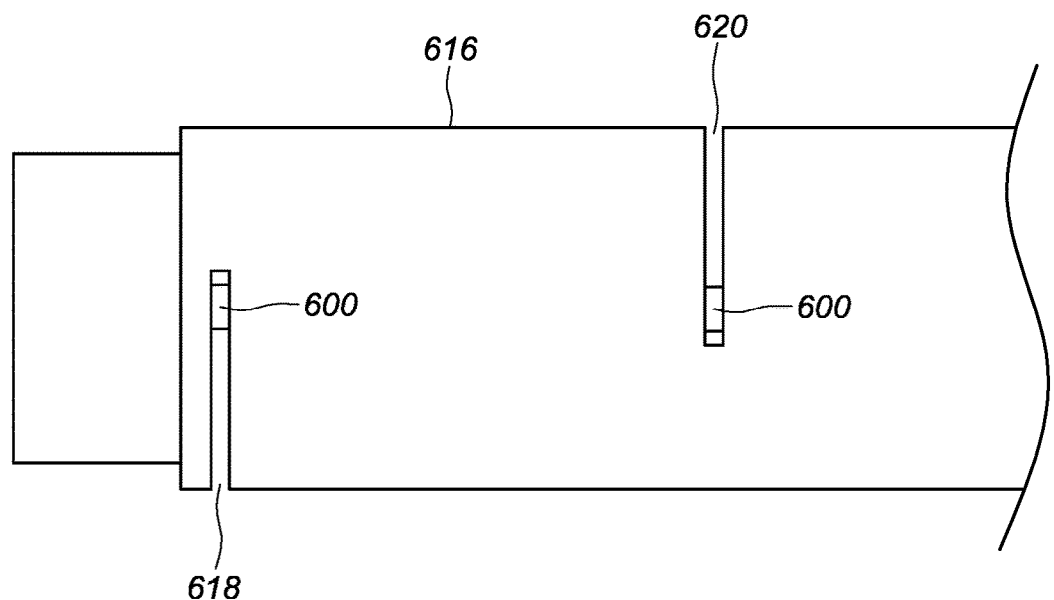
FIG. 6E is a side view of the embodiment of a flexing structure illustrated in FIG. 6D.

FIG. 6E depicts a side view of the flexing structure 616 depicted in FIG. 6D. The flexing structure 616 can comprise a plurality of slots 618, 620 to accommodate bending of the flexing structure 616 in response to contact with a distal end of a catheter.

Figure 6F:
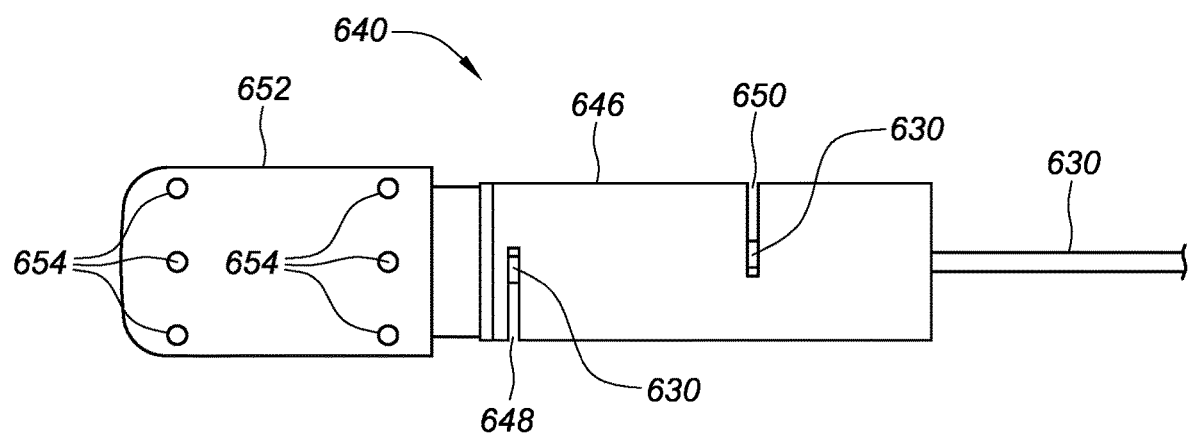
FIG. 6F is a side view of one embodiment of a tip assembly comprising a flexing structure.

FIG. 6F depicts a side view of another embodiment of a catheter tip assembly 640. The catheter tip assembly 640 can comprise a flexing structure 646, a catheter tip 652, a first slot 648, a second slot 650, and a multi-core fiber 630. The flexing structure 646 can be positioned relative to the catheter tip 652, such as an ablation and/or mapping tip. The catheter tip 652 can comprise a plurality of irrigation ports 654 to enable cooling fluid to be discharged from the catheter during a medical procedure. In one embodiment, the flexing structure 646 can be located proximate the catheter tip 652.

Figures 7A, 7B:
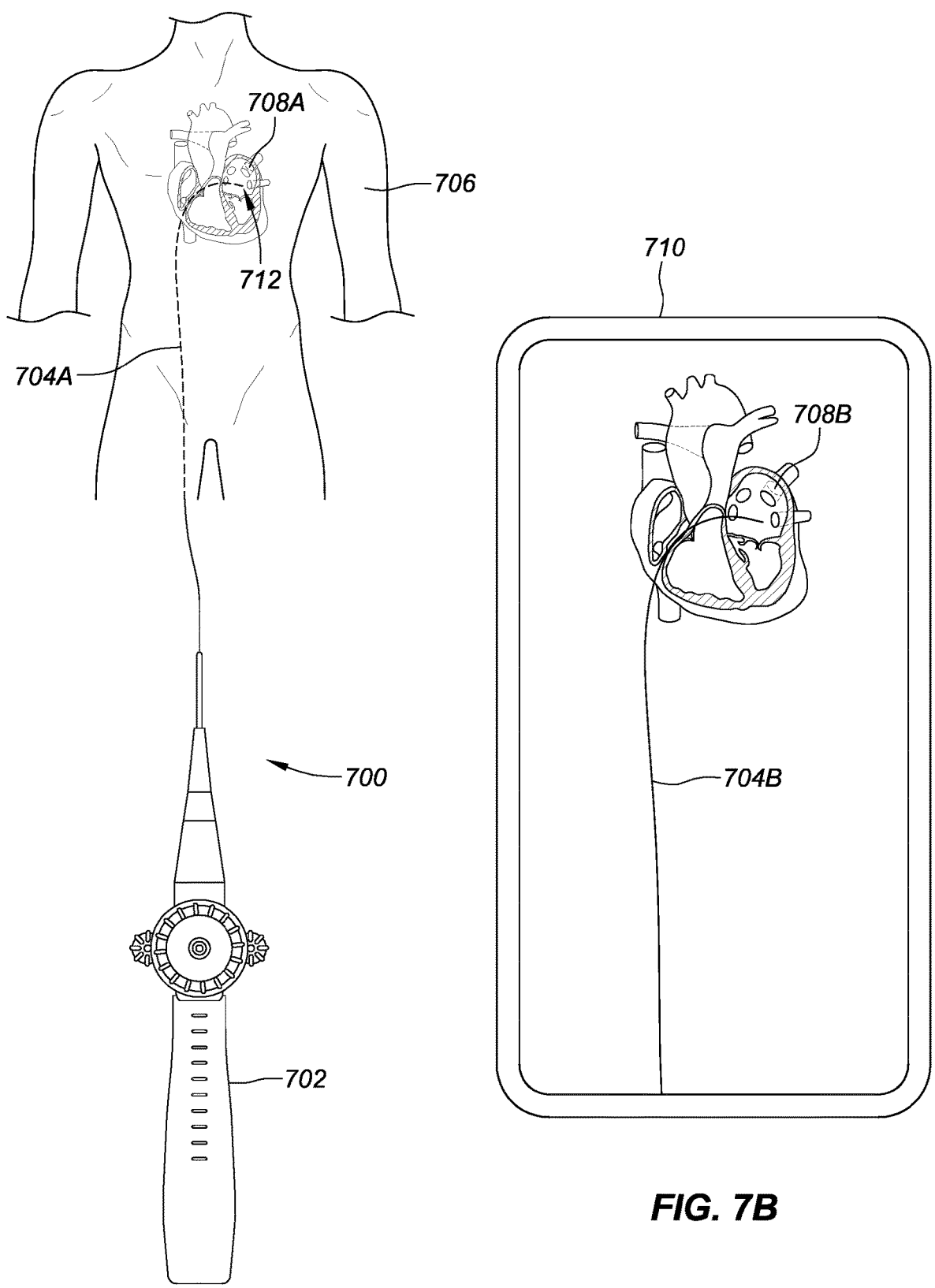
FIG. 7A is a diagrammatic view of catheter comprising a multi-core fiber during a procedure.
FIG. 7B is a diagrammatic view of a display depicting a catheter shaft.

The shape sensors in the multi-core fiber can be implemented in a medical device, such as a catheter. FIG. 7A illustrates an exemplary catheter, which is a cardiac ablation catheter 700 in the illustrated embodiment. The catheter 700 may include a handle 702 for manual operation, or in other embodiments may be implemented in a robotic system (not shown). The catheter 700 includes a catheter shaft 704A, which may be guided through the vasculature of a patient's body 706 to the patient's heart 708A. Using the fiber Bragg grating shape sensing sensors (e.g., 602, 604, 606 of FIGS. 6A-6C) provided via a multi-core fiber (e.g., 600 of FIGS. 6A-6C) provided within the shaft 704A, the shape of the catheter shaft 704A can be detected and visually recreated as shown by depicted shaft 704B shown in FIG. 7B. For example, as shown in FIG. 7B, the depicted shaft 704B, as well as a depicted patient's heart 708B, may be presented on a display 710.

Additionally, using the fiber Bragg grating force sensors (e.g., 608, 610, 612 of FIGS. 6A-6C) provided via the multi-core fiber (e.g., 600 of FIGS. 6A-6C) provided within the shaft 704A, the varying force impacting the tip 712 of the shaft 704A can be detected as a result of varying degrees of contact with the tissue of the heart 708A.

In this manner, the catheter shaft 704A may be viewed as the depicted catheter shaft 704B via the display 710, while the degree of contact force on the catheter tip 712 can be concurrently or alternately monitored.

An embodiment of a medical device incorporating such principles includes a manipulatable catheter having a shaft that has distal and proximal portions relative to the manipulating mechanism(s). Within the shaft is a multi-core optical fiber, having a plurality of optical cores dedicated for shape sensing sensors, and a plurality of optical cores dedicated for force sensing sensors.

In a more particular embodiment, at least one of the cores of the multi-core optical fiber is dedicated for temperature compensation, which is used to adjust sensed values obtained from the shape sensing sensors and/or the force sensing sensors. In one embodiment, the shape sensing sensors are implemented using one or more fiber Bragg gratings, which reflect light in a perceivable manner when deflected. In another embodiment, the force sensing sensors are implemented using one or more fiber Bragg gratings, which also reflect light in a perceivable manner when deflected. Other embodiments implement fiber Bragg grating technology for both the force sensing and shape sensing sensors, where in yet another embodiment the temperature sensing core also utilizes fiber Bragg grating technology.

One embodiment involves utilizing the multi-core fiber to accommodate only force sensors for detecting distal portion contact with tissue, while in another embodiment the multi-core fiber is utilized to accommodate only shaft shape sensors.

In one embodiment where the multi-core fiber accommodates cores for both shape and force sensing, the shape and force sensing cores are staggered from one another such that every other core is devoted to shape sensors, and the other cores are devoted to force sensors. In one particular embodiment, this staggered pattern is substantially symmetric, and in still another embodiment a core to accommodate one or more temperature sensors (e.g., fiber Bragg grating) is positioned substantially centrally in the fiber relative to the surrounding, symmetric force and shape sensing cores.

Any manner of enabling deflection of the shaft and catheter tip may be utilized. In one embodiment, a flexing structure is provide proximate the force sensors in respective cores of the multi-core fiber to enable the distal portion of the catheter, and thus the included fiber, to deflect. This deflection is perceivable by the fiber Bragg grating or other sensors to provide an indication of an amount of force impacting the distal portion of the catheter.

Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

Further, although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

What is claimed is:

1. A catheter assembly comprising:
    a catheter tip assembly coupled to a distal end of a catheter body, the catheter tip assembly comprising:
        a flexing structure configured to bend in response to an external force;
        an electrode adjacent the flexing structure, the electrode comprising:
            a distal end wall; and
            a longitudinally extending inner wall intersecting with the distal end wall,
            wherein the distal end wall and the inner wall define a cavity; and
        a multi-core fiber comprising a plurality of cores and a distal end, wherein each of the plurality of cores extends from a proximal end to the distal end of the multi-core fiber, wherein at least one of the plurality of cores comprises a fiber Bragg grating and is configured to sense a shape of the flexing structure,
    wherein the distal end of the multi-core fiber is disposed within the cavity and is in contact with a surface of the distal end wall of the electrode, and
    wherein a distal end of the fiber Bragg grating is disposed within the cavity and is spaced apart from the distal end wall of the electrode.

2. The assembly of claim 1, wherein the plurality of cores includes a core configured to sense a force imparted on the flexing structure.

3. The assembly of claim 2, wherein the core configured to sense the force uses different optical sensing from the fiber Bragg grating.

4. The assembly of claim 1, wherein the at least one of the plurality of cores includes a common core configured to sense the shape of the flexing structure and a force imparted on the flexing structure.

5. The assembly of claim 4, wherein the common core includes shape sensing gratings and force sensing gratings, the shape sensing gratings configured to operate with light at a first frequency, and the force sensing gratings configured to operate with light at a second frequency different from the first frequency.

6. The assembly of claim 1, wherein the flexing structure comprises a deformation mechanism.

7. The assembly of claim 1, wherein an end surface of the plurality of cores is amalgamated.

8. The assembly of claim 1, wherein a distal end of the plurality of cores is crushed.

9. The assembly of claim 1, wherein the multi-core fiber comprises a first set of gratings and a second set of gratings, the first set of gratings configured to be bent, and the second set of gratings configured to be axially compressed.

10. The assembly of claim 1, wherein the multi-core fiber comprises three shape sensing cores.

11. A catheter assembly comprising:
a catheter tip assembly coupled to a distal end of a catheter body, the catheter tip assembly comprising:
   a flexing structure configured to bend in response to an external force;
   a catheter tip adjacent the flexing structure, the catheter tip comprising:
      a distal end wall; and
      a longitudinally extending inner wall intersecting with the distal end wall,
      wherein the distal end wall and the inner wall define a cavity; and
   a multi-core fiber comprising a plurality of cores and a distal end, wherein each of the plurality of cores extends from a proximal end to the distal end of the multi-core fiber, wherein at least one of the plurality of cores comprises a fiber Bragg grating and is configured to sense a shape of the flexing structure,
wherein the distal end of the multi-core fiber is disposed within the cavity and is in contact with a surface of the distal end wall of the catheter tip.

12. The assembly of claim 11, wherein the plurality of cores includes a core configured to sense a force imparted on the flexing structure.

13. The assembly of claim 12, wherein the core configured to sense the force uses different optical sensing from the fiber Bragg grating.

14. The assembly of claim 11, wherein the at least one of the plurality of cores includes a common core configured to sense the shape of the flexing structure and a force imparted on the flexing structure.

15. The assembly of claim 14, wherein the common core includes shape sensing gratings and force sensing gratings, the shape sensing gratings configured to operate with light at a first frequency and the force sensing gratings configured to operate with light at a second frequency different from the first frequency.

16. The assembly of claim 11, wherein the flexing structure comprises a deformation mechanism.

17. The assembly of claim 11, wherein an end surface of the plurality of cores is amalgamated.

18. The assembly of claim 11, wherein a distal end of the plurality of cores is crushed.

19. The assembly of claim 11, wherein the multi-core fiber comprises a first set of gratings and a second set of gratings, the first set of gratings configured to be bent, and the second set of gratings configured to be axially compressed.

20. The assembly of claim 11, wherein the multi-core fiber comprises three shape sensing cores.

* * * * *